United States Patent
Chen et al.

(10) Patent No.: US 7,792,392 B2
(45) Date of Patent: Sep. 7, 2010

(54) FIBER OPTIC GAS SENSOR

(75) Inventors: Peng Chen, Wexford, PA (US); Michael P. Buric, Pittsburgh, PA (US); Philip R. Swinehart, Columbus, OH (US); Mokhtar S. Maklad, Westerville, OH (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 164 days.

(21) Appl. No.: 11/957,746

(22) Filed: Dec. 17, 2007

(65) Prior Publication Data

US 2009/0129721 A1    May 21, 2009

Related U.S. Application Data

(60) Provisional application No. 60/870,431, filed on Dec. 18, 2006.

(30) Foreign Application Priority Data

Dec. 9, 2006 (DE) .................. 10 2006 058 138

(51) Int. Cl.
  *G02B 6/00* (2006.01)
  *G02B 6/34* (2006.01)
(52) U.S. Cl. .................. 385/12; 385/13; 385/37
(58) Field of Classification Search ............ 385/12, 385/13, 37
  See application file for complete search history.

(56) References Cited

U.S. PATENT DOCUMENTS

| | | | | |
|---|---|---|---|---|
| 3,927,555 A | * | 12/1975 | Godwin et al. | 73/31.01 |
| 5,280,172 A | * | 1/1994 | Di Bin et al. | 250/227.21 |
| 6,185,344 B1 | * | 2/2001 | Bevenot et al. | 385/12 |
| 6,897,960 B2 | * | 5/2005 | DiMeo et al. | 356/437 |
| 7,521,252 B2 | * | 4/2009 | Carpenter et al. | 436/144 |
| 2003/0218124 A1 | | 11/2003 | Johnson et al. | |

(Continued)

OTHER PUBLICATIONS

"The characterization hydrogen sensors based on Palladium electroplated fiber Bragg gratings (FBG)", by Peng et al, SPIE conference of Sensory Phenomena and measurement Instrumentation for Smart Structures and Materials, Mar. 1999, vol. 3670, pp. 42-53.*

(Continued)

*Primary Examiner*—Charlie Peng
*Assistant Examiner*—Robert Tavlykaev
(74) *Attorney, Agent, or Firm*—Eckert Seamans Cherin & Mellott, LLC; Philip E. Levy, Esq.

(57) ABSTRACT

A gas sensor includes an in-fiber resonant wavelength device provided in a fiber core at a first location. The fiber propagates a sensing light and a power light. A layer of a material is attached to the fiber at the first location. The material is able to absorb the gas at a temperature dependent gas absorption rate. The power light is used to heat the material and increases the gas absorption rate, thereby increasing sensor performance, especially at low temperatures. Further, a method is described of flash heating the gas sensor to absorb more of the gas, allowing the sensor to cool, thereby locking in the gas content of the sensor material, and taking the difference between the starting and ending resonant wavelengths as an indication of the concentration of the gas in the ambient atmosphere.

12 Claims, 20 Drawing Sheets

U.S. PATENT DOCUMENTS

2004/0173004 A1    9/2004    Eblen, Jr. et al.
2005/0163424 A1*   7/2005    Chen ........................... 385/37

OTHER PUBLICATIONS

"Hydrogen sensor based on a palladium-coated fibre-taper with improved time-response," by Zalvidea et al, Sensors and Actuators B, vol. 114, 2006, pp. 268-274, available online since Jul. 22, 2005.*

Voet et al., 17th International Conference on Optical Optical Fibre Sensors, May 23-27, 2005, vol. 5855, 6 pp.

Lundstrom et al., "A Hydrogen-Sensitive MOS Field-effect Transistor", Applied Physics Letters, vol. 26, No. 2, Jan. 15, 1975 pp. 55-57.

Steele et al., "Palladium/Cadmium-Sulfide Schottky Diodes for Hydrogen Detection", Applied Physics Letters, vol. 28, No. 11, Jun. 1, 1976, pp. 687-688.

D'Amico et al., "Palladium-Surface Acoustic Wave Interaction for Hydrogen Detection", Appl. Phys. Lett. 41(3), Aug. 1, 1982, pp. 300-301.

Villatoro et al., "Fast Detection of Hydrogen with Nano Fiber Tapers Coated with Ultra Thin Palladium Layers", Optics Express, Jun. 27, 2005, vol. 13, No. 13, pp. 5087-5092.

Tabib-Azar et al., "Highly Sensitive Hydrogen Sensors Using Palladium Coated Fier Optics with Exposed Cores and Evanescent Field Interactions", Sensors and Actuators B 56 (1999) 158-163.

Bevenot et al., "Surface Plasmon Resonance Hydrogen Sensor Using an Optical Fibre", Meas. Sci. Technol. 13 (2002) 118-124.

Bevenot et al., "Hydrogen Leak Detection using an Optical Fibre Sensor for Aerospace Applications", Sensors and Actuators B 67 (2000) 57-67.

M.A. Butler, "Optical Fiber Hydrogen Sensor", Appl. Phys. Lett. 45(10), Nov. 15, 1984, pp. 1007-1009.

Favier et al., "Hydrogen Sensors and Swtiches from Electrodeposited Palladium Mesowire Arrays", Science 193, 2227 (2001); DOI: 10.1126science.1063189, pp. 2227-2231.

Sekimoto, "A Fiber-Optic Evanescent-Wave Hydrogen Gas Sensor Using Palladium-Supported Tungsten Oxide", Sensors and Actuators B 66 (2000) 142-145.

* cited by examiner

FIBER OPTIC GAS SENSOR

CROSS-REFERENCE TO RELATED APPLICATION

This application claims the benefit of U.S. Provisional Application No. 60/870,431 entitled "Active Fiber Bragg Grating Hydrogen Sensors For All-Temperature Operation," which was filed on Dec. 18, 2006.

GOVERNMENT CONTRACT

This work was supported in part by a grant from NASA under SBIR Contract No. NNC06CA52C. The United States government may have certain rights in the invention described herein.

BACKGROUND OF THE INVENTION

1. Field of the Invention

The present invention relates to sensors for sensing the presence of gasses such as hydrogen, and more specifically to fiber optic gas sensor that employs an in-fiber resonant wavelength device, such as an FBG, wherein performance is improved using an in-fiber power light.

2. Description of Related Art

Fiber optic components, such as, without limitation, Fiber Bragg Gratings (FBGs), fiber interferometers, and Fabry-Perot cavities (FPs) are well known and are key components used in many optical communication and sensing applications. For example, such components are often utilized in constructing multiplexers and de-multiplexers used in wavelength division multiplexing (WDM) optical communications systems, and in constructing optical strain sensors, temperature sensors, pressure or vibration sensors, chemical sensors and accelerometers. In-fiber optic components, meaning those provided in or as part of an optical fiber, offer several important advantages over other optical and electronic devices, including low manufacturing cost, immunity to electromagnetic radiation and changing (often harsh) ambient conditions, an explosive-proof and in-vivo safe nature, long lifetime, and high sensitivity.

Historically, in-fiber optic components have been passive, meaning they cannot be actively adjusted and/or reconfigured once deployed to, for example, adopt new network topologies or adjust sensing parameters including sensitivity, set point, triggering time, dynamic range and responsivity. In addition, passive in-fiber optic components require delicate and costly packaging to eliminate temperature drifting. These facts have, despite the advantages described above, limited the performance and use of in-fiber components. As a result, work has been done to develop tunable in-fiber optic components, such as a tunable FBG. As is known in the art, an FBG consists of a series of perturbations, forming a grating from periodic variations in the index of refraction along the length of an optical fiber, that will be here termed "grating elements". An FBG reflects a spectral peak of a light back through the fiber toward the light source, and the particular spectral peak (called the resonance wavelength) that is reflected depends upon the grating spacing. A corresponding valley is transmitted forward though the fiber. Thus, changes in the length of the fiber due to heat, tension or compression will change the spacing of the grating index of refraction variations (and to a lesser extent, the grating component indices of refraction) and thus the wavelength of the light that is reflected.

A typical prior art implementation of an FBG is shown in FIG. 1, and includes optical fiber 5 having core 10 surrounded by cladding 15, wherein the core 10 is provided with a grating 20. The light transmitted through optical fiber 5 and reflected by grating 20 is shown by the arrow in FIG. 1. The grating 20 shown in FIG. 1 has a constant period, $\Lambda$, meaning the grating elements are evenly spaced, and is referred to as a uniform FBG. FBGs may also include gratings that have a varying period. Such FBGs are referred to as chirped FGBs, and reflect multiple spectral peaks or a wide spectrum of light. Long period gratings, in which the spacing is large compared to the core diameter, and apodized gratings are also useful. Tuning mechanisms (for changing the fiber length and other characteristics such as refractive index) that have been previously explored for FBGs and other in-fiber optic components include on-fiber electrical heating, piezoelectric actuators, mechanical stretching and bending, and acoustic modulation. The problem has been that each of these tuning mechanisms requires an energy source for operation, which, to date, has been electrical. In particular, electrical cable must be run with the optical fiber to provide current for on-fiber heating elements, to supply voltages to drive piezoelectric actuators, to drive stepper motors to stretch and bend the fibers, or to initialize acoustic waves. Additional cabling of this sort is problematic, as it, among other things, typically increases manufacturing costs, is bulky, is not immune to electromagnetic radiation, is difficult to embed in materials and structures, and typically has a shorter lifetime than the associated, normally durable optical fibers.

Thus, there is a need for a mechanism for powering and tuning in-fiber optic components that does not require additional electrical cabling. Such a mechanism would allow fiber optic systems to take advantage of the improved performance and functionality of in-fiber optic components without the disadvantages and drawbacks presented by electrical cabling.

Moreover, hydrogen is becoming an attractive alternative fuel source for use in clean-burning engines and power plants. Some mission-critical applications such as the Space Shuttle engine already employ liquid hydrogen as a fuel. Unfortunately, the use of highly flammable liquid $H_2$ also introduces a number of safety concerns due to its rapid evaporation rate and low explosive limit. In order to mitigate the high risk of explosion due to leaks in hydrogen fueled systems, an efficient system of $H_2$ leak detection is needed. Such a system should allow detection well below the 4% mass concentration explosion limit of hydrogen.

Recently, various electrical sensors based on the change of resistivity of palladium (Pd) have been developed including some nano-scale devices. Examples of such sensors are described in A. D'Amico et al, "Palladium-surface acoustic wave interaction for hydrogen detection," Appl. Phys. Lett., vol. 41, pp. 300-301, (1982); I. Lundstrom et al., "A hydrogen-sensitive MOS field-effect transistor," Appl. Phys. Lett., vol. 26, pp. 55-57, (1975); and M. C. Steele et al., "Palladium/cadmium-sulfide Schottky diodes for hydrogen detection," Appl. Phys. Lett. vol. 28, pp. 687-688, (1976). Furthermore, because of their explosion proof nature, the desirability of fiber optic sensors has been recognized in recent years and more emphasis has been placed on the development of optical sensors such as those described in M. Tabib-Azar et al., "Highly sensitive hydrogen sensors using palladium coated fiber optics with exposed cores and evanescent field interactions," Sens. Act., vol. B 56, pp. 158-163, (1999); J. Villatoro et al., "Fast detection of hydrogen with nano fiber tapers coated with ultra thin palladium layers," Optics. Exp., vol. 13, pp. 5087-5092, (2005); J. Villatoro et al., "In-Line Highly Sensitive Hydrogen Sensor Based on Palladium-Coated Single-Mode Tapered Fibers," IEEE Sens. Journal, vol. 3, pp. 533-537 (2003); and X. Bevenot et al., "Surface plasmon resonance hydrogen sensor using an optical fibre," IOP Meas. Sci. Technol., vol. 13, pp. 118-124, (2002). Of particular interest are optical sensors that are of the type that can be interrogated remotely over long fibers, such as those described in X. Bevenot et al., "Hydrogen leak detection using an optical fibre sensor for aerospace applications," Sens. Act., vol. B 67, pp. 57-67, (2000); A. Trouillet et al., "Fibre gratings for hydrogen sensing," Measurement Science & Technol., vol. 17(5), pp. 1124-1128, (2006); and J. A. Guemes et al., "Comparison of three types of fibre optic hydrogen sensors within the frame of CryoFOS project," Third International Conference on Experimental Mechanics and Third Conference of the Asian Committee on Experimental Mechanics, Proceedings of the SPIE, Vol. 5855, pp. 1000-1003 (2005). Another significant advantage of fiber-based hydrogen sensors is the capability of providing numerous sensing points in order to generate data regarding the location of the leak itself.

One of the most important requirements for any leak detection system, particularly one for detecting hydrogen leaks, is the ability to operate over a large range of temperatures (e.g., for use near extremely cold liquid-$H_2$ tanks and pipes, as well as in much warmer environments). In addition, with any leak-detection system, response time is paramount to successfully averting disaster. Although a number of sensing solutions have been developed based on the use of a Pd-coating as described above, those solutions share a common problem, namely, due to palladium's slow hydrogen absorption rate at low temperature (e.g., on the order of 20 degrees C. and lower), the sensors exhibit an extremely low sensitivity and slow response time at low temperatures. Thus, there is a need for a fiber optic sensing solution that exhibits improved sensitivity and response time at low temperatures.

SUMMARY OF THE INVENTION

The present invention, in one embodiment, provides a sensor for sensing a gas, such as hydrogen, that includes an optical fiber having a core and a wavelength resonant in-fiber optic component, such as a fiber Bragg grating or Fabry-Perot filter, provided in the core at a first location. The optical fiber propagates a sensing light and a power light, with the sensing light being propagated in the core. The wavelength resonant in-fiber optic component receives the sensing light and reflects a reflected light having a resonance wavelength that is dependent on a characteristic, such as a grating spacing, of the wavelength resonant in-fiber optic component. The reflected light is used to determine at least one of a presence of and a concentration of the gas. In addition, at least one layer of a certain material is attached to the optical fiber in proximity to the first location. In particular, the material is a material, such as palladium or a palladium alloy, that is able to absorb the gas being sensed (e.g., hydrogen) at a temperature dependent gas absorption rate that increases when a temperature of the material is increased up to some limiting high temperature that is dependent on environmental conditions. The material induces a strain in the optical fiber when the material absorbs the gas, with a magnitude of the strain being dependent upon an amount of the gas that is absorbed. The strain in the optical fiber changes the characteristic, e.g., grating spacing. Finally, the optical fiber is structured to allow at least a portion of the power light to be used to heat the material. In one particular embodiment, the optical fiber is structured to allow at least a portion of the power light to be released from the optical fiber at the first location and be absorbed by the material. In another embodiment, at least a portion of the power light may be absorbed by another portion of the fiber, such as the inner or out cladding, generate heat that in turn heats the material. The absorbed power light heats the material and increases the gas absorption rate. As a result, the sensitivity and response time of the sensor is improved, particularly at low temperatures.

In another embodiment, the invention provides a method of sensing a gas, such as hydrogen, that includes providing an optical fiber, wherein the optical fiber has a core, a wavelength resonant in-fiber optic component, such as a fiber Bragg grating or a Fabry-Perot filter, provided in the core at a first location, and at least one layer of a material, such as palladium or an alloy of palladium, attached to the optical fiber in proximity to the first location. The material is able to absorb the gas at a temperature dependent gas absorption rate that increases when the temperature of the material is increased. The material induces a strain in the optical fiber when the material absorbs the gas, with a magnitude of the strain being dependent upon an amount of the gas that is absorbed by the material. The strain changes a characteristic, e.g., the grating spacing, of the wavelength resonant in-fiber optic component. The method further includes propagating a sensing light in the core, wherein the wavelength resonant in-fiber optic component receives the sensing light and reflects a reflected light having a resonance wavelength that is dependent on the characteristic of the wavelength resonant in-fiber optic component. The method still further includes propagating a power light in the optical fiber, and using the power light to directly or indirectly heat the material and therefore increase the gas absorption rate. This may include causing at least a portion of the power light to be released from the optical fiber at the first location and be absorbed by the material. The absorbed power light heats the material and increases the gas absorption rate. Finally, the method includes using the reflected light to determine at least one of a presence of and a concentration of the gas.

In yet another embodiment, the invention provides a method of sensing a gas at an ambient temperature that includes providing an optical fiber, wherein the optical fiber has a core, a wavelength resonant in-fiber optic component provided in the core at a first location, and at least one layer of a material attached to the optical fiber in proximity to the first location. The material is able to absorb the gas at a temperature dependent gas absorption rate that increases when a temperature of the material is increased. The method further includes propagating a first sensing light in the core at the ambient temperature, wherein the wavelength resonant in-fiber optic component receives the first sensing light and reflects a first reflected light having a first resonance wavelength that is dependent on an ambient characteristic of the wavelength resonant in-fiber optic component. Also, the method includes propagating a power light in the optical fiber for a defined period of time during which at least a portion of the power light is used to directly or indirectly heat the material. In one embodiment, at least a portion of the power light is released from the optical fiber at the first location and absorbed by the material, wherein the absorbed power light heats the material. Alternatively, the power light may be absorbed by another portion of the fiber, such as a cladding layer or even the core, which in turn causes heat to be generated which heats the material. The heating of the material causes the material to induce a strain in the optical fiber that changes the ambient characteristic to a changed characteristic. The method still further includes allowing the material to cool to a temperature substantially equal to the ambient temperature after the defined period of time has expired, and propagating a second sensing light in the core after the material is allowed to cool, wherein the wavelength resonant in-fiber optic component receives the second sensing light and reflects a second reflected light having a second resonance wavelength that is dependent on the changed characteristic. Finally, the method includes determining a difference between the first resonance wavelength and the second resonance wavelength, and using the difference to determine at least one of a presence of and a concentration of the gas.

BRIEF DESCRIPTION OF THE DRAWINGS

These and other advantages of the present invention will become readily apparent upon consideration of the following detailed description and attached drawings, wherein.

DETAILED DESCRIPTION OF THE PREFERRED EMBODIMENTS

The present invention relates to various systems and methods for providing active in-fiber optic components that are powered by in-fiber light. Specifically, as described in greater detail herein, various optical fibers are provided that propagate both a sensing or signal light and a power light wherein the power light is used to provide the energy required to tune the in-fiber optic component.

Figure 2A:
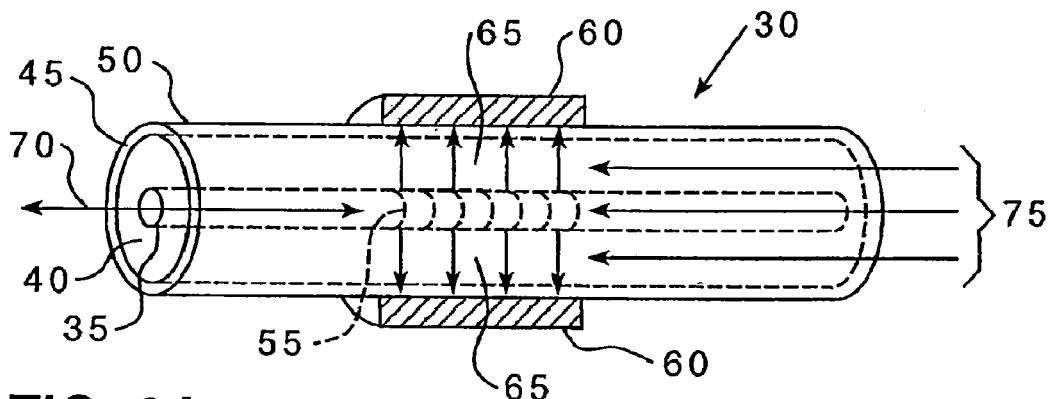
FIGS. 2A and 2B are a partial cross-sectional side view and a side view, respectively, of an optical fiber having a tunable in-fiber optic component according to one embodiment of the present invention.
Figure 2B:
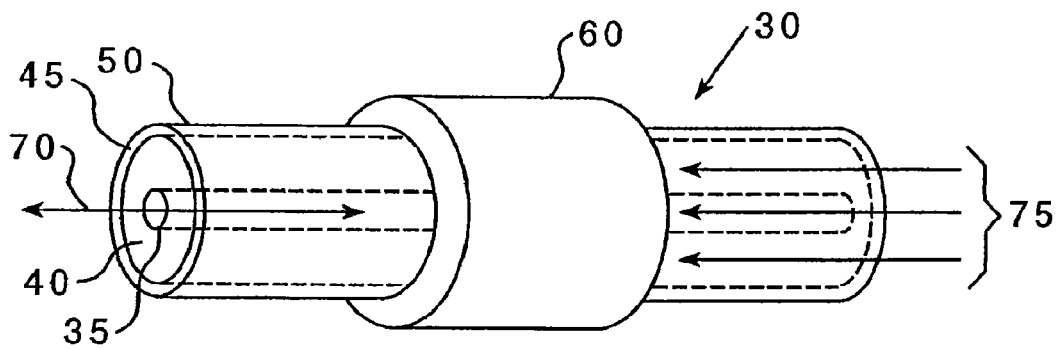
Figure 3:
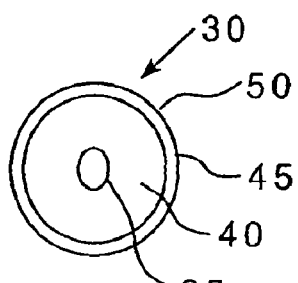
FIG. 3 is a cross-sectional end view of the optical fiber shown in FIGS. 2A and 2B.

FIGS. 2A and 2B are side views (2A in partial cross-section) and FIG. 3 is a cross-sectional end view of optical fiber 30 according to one embodiment of the present invention. As seen most readily in FIG. 3, optical fiber 30 includes a core 35, inner cladding 40, outer cladding 45 and protective layer 50. Preferably, core 35, inner cladding 40 and outer cladding 45 are made of light propagating materials, wherein core 35 has an index of refraction that is greater than the index of refraction of inner cladding 40, which in turn is greater than the index of refraction of outer cladding 45. Except as otherwise described herein, establishing the relative indices of refraction in this manner causes light propagating in core 35 to be confined therein, and light propagating in inner cladding 40 to be confined therein. Inner cladding 40 and outer cladding 45 may be formed by a number of known techniques, such as modified chemical vapor deposition (MCVD). The thickness of outer cladding 45 is preferably about 10 μm to allow for convenient optical tap region fabrication as described elsewhere herein. In addition, inner cladding 40 and outer cladding 45 should be highly transparent.

In one particular embodiment, core 35 is made of a glass material such as fused silica that is doped with germanium and/or boron to increase the index of refraction thereof, inner cladding 40 is made of fused silica, and outer cladding 45 is made of fused silica that is doped with fluorine (preferably 3-mole % fluorine) to decrease the index of refraction thereof. Preferably, core 35 is doped to achieve an N.A. value of about 0.16, which is slightly higher than the N.A. value of 0.13 for standard telecommunications fibers. Both pure silica and fluorine-doped silica are transparent to UV light, which allows uniform penetration of KrF 248 nm laser radiation for in-fiber FBG fabrication. In one particular example of this particular embodiment, core 35 has an index of refraction equal to about 1.45, inner cladding 40 has an index of refraction equal to about 1.445, and outer cladding 45 has an index of refraction equal to about 1.44. In addition, in another specific example, core 35 has an elliptical shape with an 8 μm major axis and a 5 μm minor axis, inner cladding 40 has an outer diameter equal to about 105 μm, and outer cladding 45 has an outer diameter equal to about 125 μm. Alternatively, outer cladding 45 may be made of a polymer such as clear silicone or PFA. Preferably, core 35 is a polarization-maintaining ellipse with a beat length of less than 4 mm at 1550 nm to ensure high sensing sensitivity and to reduce polarization phase noise. Other core and cladding sizes and shapes are possible without limitation.

Referring to FIGS. 2A and 2B, optical fiber 30 includes an in-fiber optic component 55 such as, for example, an FBG (shown in FIG. 2A). In addition, an optical transducing element is located in a position that is proximate to a portion of optical fiber 30. In the embodiment shown in FIGS. 2A and 2B, the optical transducing element is a light absorbing thermal coating 60 provided around at least a portion of and preferably the entirety of the outer circumference of optical fiber 30 (FIG. 2A shows thermal coating 60 in partial cut-away to enable viewing of the other components of optical fiber 30). According to one particular embodiment, thermal coating 60 is a metal film, such as, for example, a silver, nickel, titanium or other light absorbing metal film, that is deposited on the outside of optical fiber 30 (protective layer 50 is removed at this location for reasons that will be clear below and thermal coating 60 is applied to outer cladding 45) by any one of many known coating methods such as plating, sputtering and e-beam thermal evaporation. The thickness of thermal coating 60 is preferably on the order of about 10 nm to tens of microns. A key characteristic of thermal coating 60 is that is heats up and radiates and/or conducts heat when exposed to certain types of light from inside optical fiber 30. Other suitable materials such as, without limitation, light absorbing polymers, carbon, semiconductors, ceramics, light absorbing doped glasses, metal films of any kind, metal oxides, metal nitrides, and metal carbides, may be used for thermal coating 60.

Referring to FIG. 2A, optical fiber 30 also includes an optical tap region 65 located in a portion of optical fiber 30 that is proximate to thermal coating 60. Optical tap region 65 is a region of optical fiber 30 that will allow certain light, as described in greater detail below, that is propagating through optical fiber 30 to leak out of (i.e., be released from) optical fiber 30 and be absorbed by thermal coating 60. Optical tap region 65 may be created in a number of ways. For example, laser techniques or ion-implantation techniques may be used to, in effect, damage inner cladding 40 in a selected region and thereby alter its index of refraction such that the power light 75 will leak out of inner cladding 40 at optical tap region 65. It is estimated that an index change of about $5 \times 10^{-3}$ to $1 \times 10^{-2}$ through outer cladding 45 will be sufficient to release the power light 75.

Preferably, a combination of deep UV laser radiation and ion implantation are used to fabricate optical tap region 65. Compaction produced by deep UV laser radiation in germanium doped cores such as core 35 produces stress in the core-cladding interface, which eventually damages the interface region and produces leaking light. For example, a combination of 157 nm $F_2$ vacuum UV lasers and 248 nm KrF deep UV lasers based on type II photosensitivity response may be used to fabricate long-period grating type optical taps. KrF lasers are well suited for fabrication of uniform optical taps for optical tap region 65 due to the relatively weak absorption of such laser light by germanosilica waveguide cores such as core 35. The type II photosensitivity can be enhanced by using known hydrogen loading techniques. In addition, anisotropic optical taps for optical tap region 65 with highly directional leaking light can readily be fabricated with 157 nm $F_2$ laser radiation. Anisotropic optical taps are convenient for leaking light collection and refocusing. For example, highly anisotropic diffused light can be easily line-focused to generate acoustic waves for active ultrasonic sensing.

Furthermore, using an amplitude mask, the pulse fluence of the optical tap fabricating laser(s) can be tailored along fiber 30 to achieve a uniform leaking light intensity. Angular uniformity of an optical tap fabricated by deep UV laser radiation can be obtained by rotating fiber 30 during laser exposure. By adjusting pulse fluence and accumulated fluence of the lasers, optical taps can be fabricated with desired tap lengths, leaking percentages, and emitting directionalities.

With respect to ion implantation, the magnitude and location of an index of refraction change in a fiber can be precisely controlled by the selected ion species, ion energy, and total ion dose. As such, the optical damage can be localized between the surface and the interface of the inner cladding 40 and the outer cladding 45. It has been learned, for example, that 21-MeV Si and 12-MeV C ions produce uniform vacancy profiles and thus uniform index profiles, while) 0.8-MeV H ions produce vacancies that are concentrated at the end of the implantation trajectory.

Alternatively, blazed Bragg gratings may be used to implement optical tap region 65 by providing a blazed grating in a core of a fiber such as core 35 shown in FIGS. 2A and 2B or in the core of a single mode fiber similar to single mode fiber portion 85 in a location that is near the thermal coating such as thermal coating 60 or 115. In such an application, both the power light and the sensing/signal light are propagated through the same core. As is known in the art, blazed Bragg gratings are fiber gratings that have grating planes that are at an angle (<90 degrees) with respect to the longitudinal axis of the fiber in which they are created. The angled nature of the gratings causes the light reflected by the blazed Bragg grating (the resonance wavelength) to be reflected at an angle with respect to the longitudinal axis of the fiber. This light (the power light) will be coupled out of the fiber core, into the surrounding cladding, and out of the fiber, where it may be absorbed by a thermal coating such as thermal coating 60 or 115. The particular blazing angles and the degree of change of the index of refraction will determine the out-coupling efficiency, and the period of the grating will determine the out-coupling wavelength.

Figure 1:
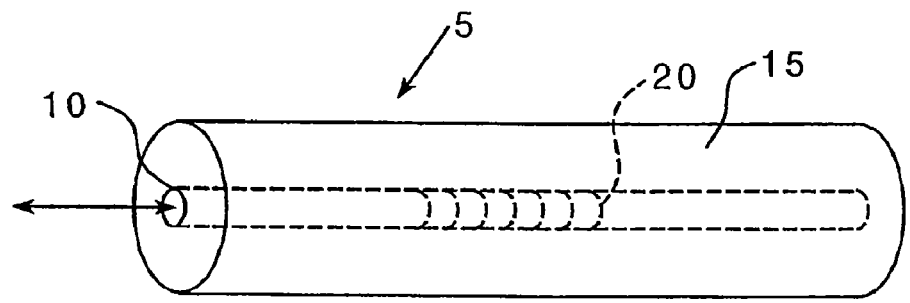
FIG. 1 is a side view of a prior art optical fiber including a Fiber Bragg Grating.

In operation, as illustrated in FIGS. 2A and 2B, a sensing light 70 is directed through and propagates through core 35. Sensing light 70 may be, for example, 1300 to 1700 nm light generated by a diode laser, such as a swept tunable laser, or a broadband source. Although the term sensing light is used herein for illustrative purposes, it will be appreciated that sensing light 70 may also be a signal propagating light used in, for example, a fiber optic communication system, and the term sensing light or sensing/signal light is intended to include signal propagating or similar lights. As is known in the art and as described elsewhere herein, sensing light 70 will propagate through core 35 and encounter in-fiber optic component 55, which, in the embodiment shown in FIG. 2A, is an FBG, and a particular resonance wavelength will be reflected back in the opposite direction. This functionality is essentially the same as described in connection with the prior art FBG shown in FIG. 1. According to an aspect of the present invention, power light 75 is simultaneously directed through both core 35 and inner cladding 40 (although power light 75 is shown propagating in a direction opposite the sensing light 70, it may also be propagated in the same direction as sensing light 70. Power light 75 may be, for example, light generated from a high-power diode laser array (not shown). Preferably, power light is on the order of 0.1 to hundreds of watts with a wavelength of between 600 nm and 1600 nm. Power light 75 will, as seen in FIGS. 2A and 2B, propagate through core 35 and inner cladding 40 and will be confined therein until it reaches optical tap region 65. When power light 75 reaches optical tap region 65, at least a portion of power light 75 will leak out of inner cladding 40 and into outer cladding 45. The portion of power light 75 that has leaked into outer cladding 45 will then be transmitted substantially radially outwardly therefrom and will ultimately be absorbed by thermal coating 60. The absorption of power light 75 will cause the temperature of thermal coating 60 to increase. As a result, thermal coating 60 will then radiate heat that is transmitted/conducted through outer cladding 45 and inner cladding 40 and into core 35. The heat in core 35 heats the in-fiber optic component 55. As is known, this heat will change (increase) the index or indexes of refraction of in-fiber optic component 55 and will, to an extent, change the size of (make larger) optical fiber 30, each of which will alter the characteristics of in-fiber optic component 55. In the case of an FBG as shown in FIG. 2A, these changes, resulting from the power light 75, will alter the resonance wavelength of the FBG. Thus, power light 75 may be used to power and tune the in-fiber optic component 55 provided in optical fiber 30. As will be appreciated, the intensity and/or duration of power light 75 may be controlled to selectively heat thermal coating 60 to produce particular changes in the in-fiber optic component 55 (e.g., particular resonance wavelengths).

Figure 4A:
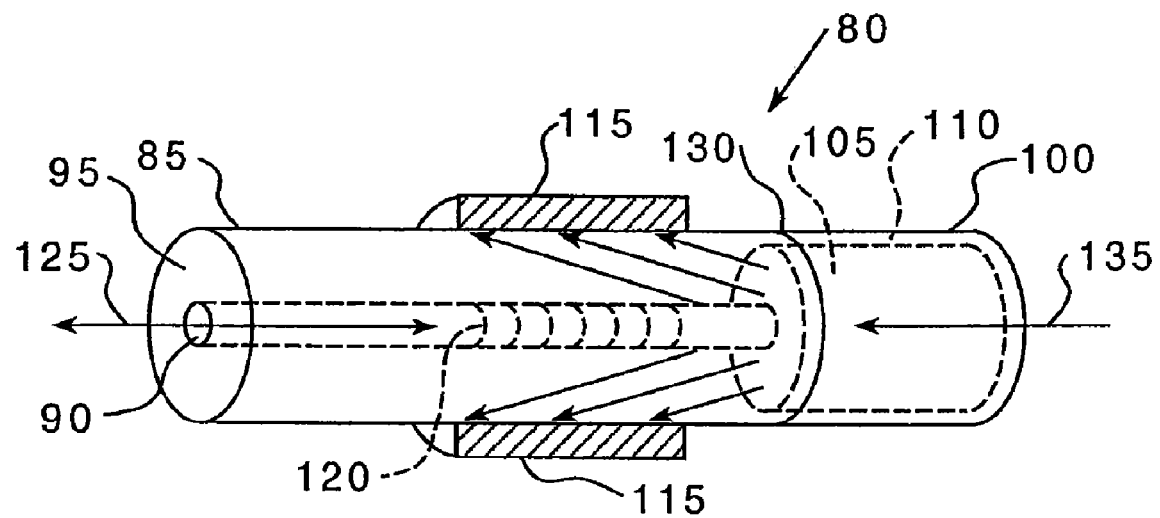
FIGS. 4A and 4B are a partial cross-sectional side view and a side view, respectively, of an optical fiber having a tunable in-fiber optic component according to an alternate embodiment of the present invention.
Figure 4B:
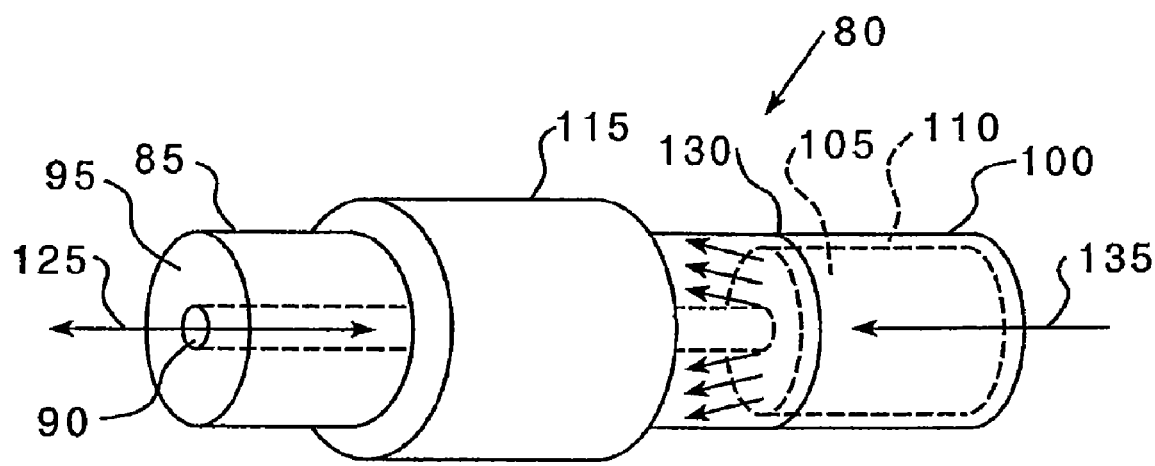

FIGS. 4A and 4B are side views (4A in partial cross-section) of optical fiber 80 according to an alternate embodiment of the present invention. Optical fiber 80 includes single mode fiber portion 85 having core 90 and cladding 95 that is joined to, such as by fusion splicing, multi-mode fiber portion 100 having core 105 and cladding 110. Single mode fiber portion 85 may be any known, commercially available single mode optical fiber material, and multi-mode fiber portion 100 may be any known, commercially available multi-mode optical fiber material. Optical fiber 80 includes an optical transducing element in the form of thermal coating 115 which is similar in structure to thermal coating 60 shown in FIGS. 2A and 2B. Optical fiber 80 also includes in-fiber optic component 120, which, in the embodiment shown in FIGS. 4A and 4B, is a uniform FBG, but may also be other types of optic components as described herein. A sensing light 125 is directed through core 90 as shown. Single mode fiber portion 85 and multi-mode fiber portion 100 are joined to one another at junction 130. As shown in FIGS. 4A and 4B, junction 130, and in particular the differing diameters of core 90 and core 105, acts as an optical tap region that allows power light 135 that is directed through and propagates through core 105 to leak out of core 105 and into cladding 95, where it is ultimately absorbed by thermal coating 115. As described in connection with FIGS. 2A and 2B, the absorbed power light 135 heats thermal coating 115 which in turn radiates heat that is conducted therefrom and heats in-fiber optic component 120, thereby changing the operating characteristics thereof.

Figure 5A:
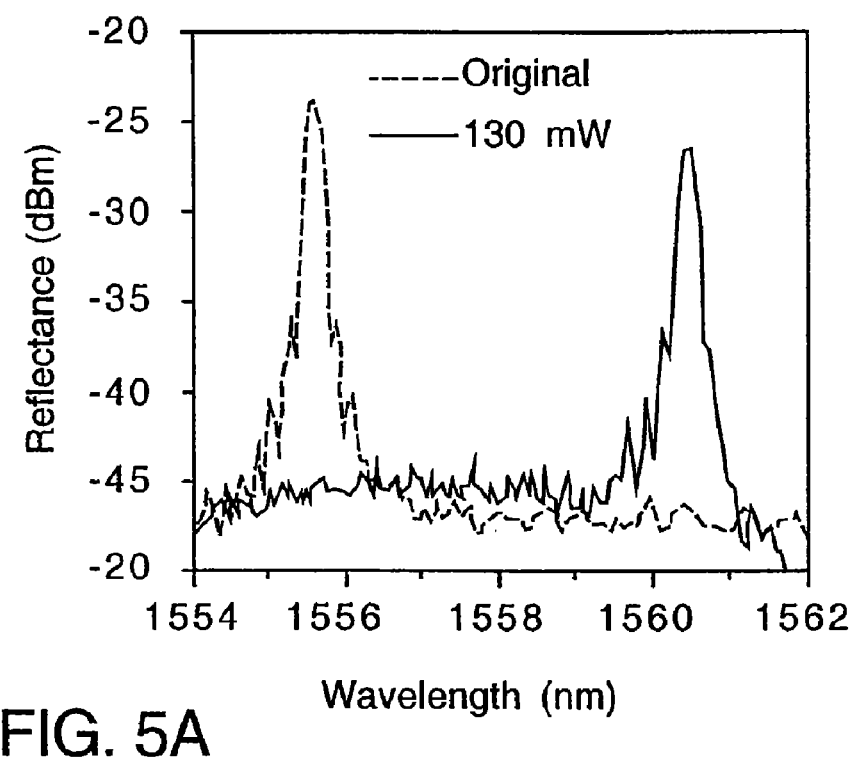
FIG. 5A is a graph illustrating a reflection spectrum shift and FIG. 5B is a graph illustrating a spectrum shift as a function of power light of a particular implementation of the optical fiber shown in FIGS. 4A and 4B.
Figure 5B:
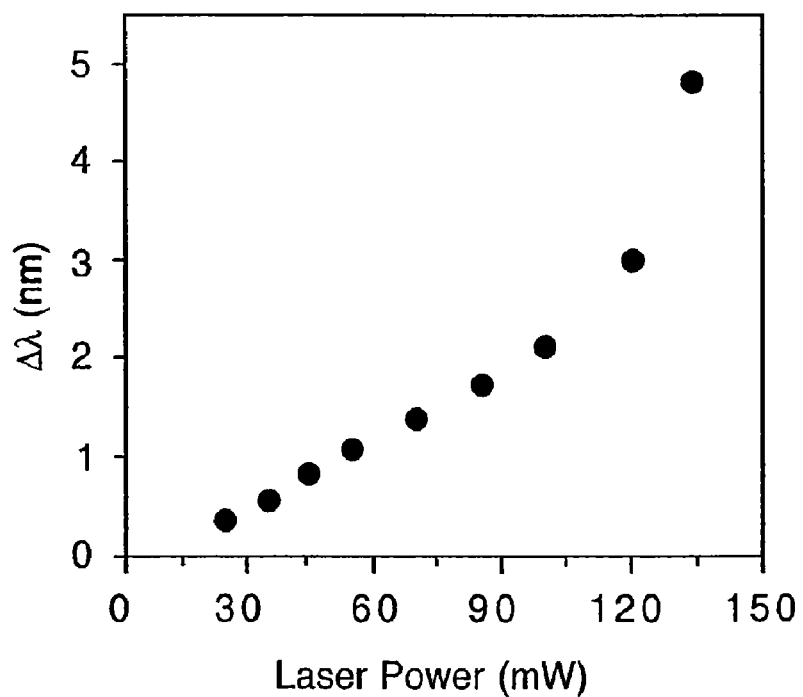

In one particular implementation investigated by the inventor, in-fiber optical component 120 consisted of several 4 mm long and 4 cm long uniform FBGs and several 4 cm long linear chirped FBGs (1 nm/cm) written into single mode fiber portion 85, which consisted of an SMF-28 fiber available from Corning Incorporated of Corning, N.Y. Single mode fiber portion 85 in this implementation consisted of a 125 μm diameter (9 μm core) fiber, and multi-mode fiber portion 100 consisted of a 140 μm diameter (100 μm core) fiber. Thermal coating 115 consisted of a 2 μm thick silver film that was positioned approximately 5 mm from junction 130. Ten watts of 910 nm laser light from a high power diode laser array was coupled into the end of multi-mode fiber portion 100 using a pair of 20× microscope objectives. The 910 nm light (power light 135) propagated through core 105 of multi-mode fiber portion 100 and leaked into cladding 95 of single mode fiber portion 85 through junction 130. The leaking power light 135 was absorbed by thermal coating 115 and raised the temperature of in-fiber optic component 120. The reflection spectra of the in-fiber optic component 120 was monitored with an optical spectrum analyzer. FIG. 5A shows a spectrum evolution of a 4 mm uniform FBG forming part of in-fiber optic component 120 heated with the power light 135 as just described. It was estimated that approximately 130 mW of power light 135 was leaked through to thermal coating 115, raising the temperature of in-fiber optic component 120 significantly and shifting the resonance wavelength as shown in FIG. 5A. FIG. 5B shows the resonance wavelength shift as a function of the input diode laser power (power light 135).

Figure 6:
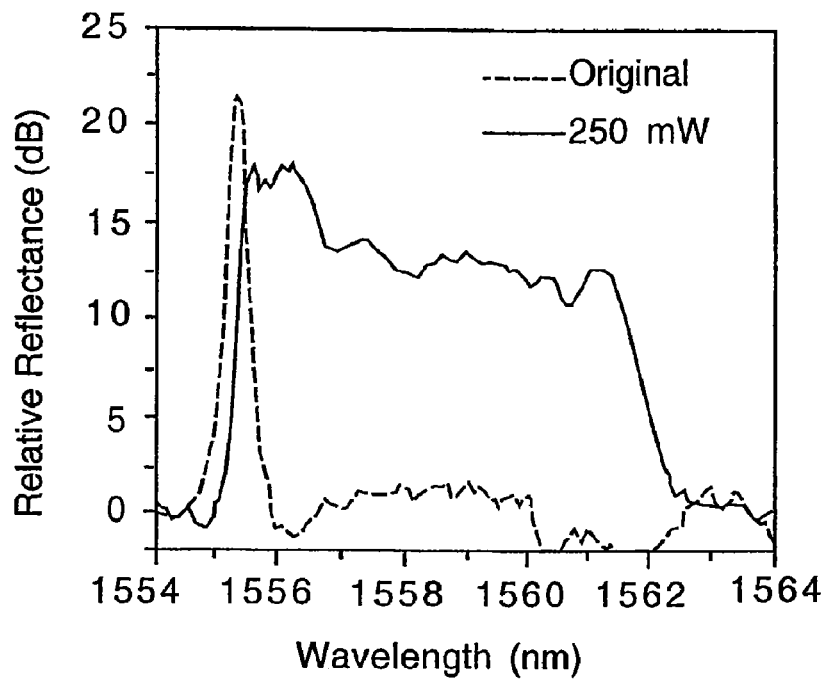
FIG. 6 is a graph illustrating a reflection spectrum expansion of a particular implementation of the optical fiber shown in FIGS. 4A and 4B.
Figure 7:
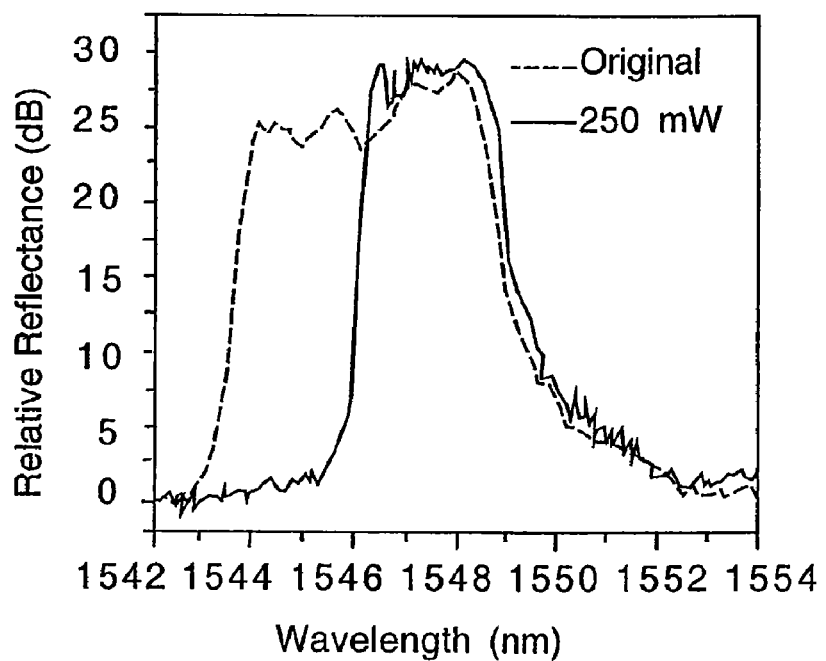
FIG. 7 is a graph illustrating a reflection spectrum compression of a particular implementation of the optical fiber shown in FIGS. 4A and 4B.

In addition, as will be appreciated, the energy of power light 135 leaking out of core 150 and being transmitted through cladding 95 falls exponentially with distance (assuming a constant loss coefficient). Thus, a temperature gradient is created along the length of thermal coating 115. In some cases, this temperature gradient is longer than the FBGs forming a part of in-fiber optic component 120. This gradient modifies the spectrum response of the FBGs and may be used to control the grating chirp and cause a spectrum stretch of the 4 cm long uniform FBG forming a part of in-fiber optic component 120. FIG. 6 shows a spectrum width stretch of a 4 cm long uniform FBG when 250 mW of diode laser light (power light 135) was directed through core 105 of multi-mode fiber portion 100 (it was estimated that approximately 120 mW of power light 135 leaked). FIG. 7, on the other hand, shows a spectrum width compression of the 4 cm linear chirped grating forming part of in-fiber optic component 120 when a 250 mW diode laser light was utilized as power light 135. In this situation, the temperature gradient created by power light 135 "de-chirped" the linear chirped grating and compressed the spectrum width.

Figure 8:
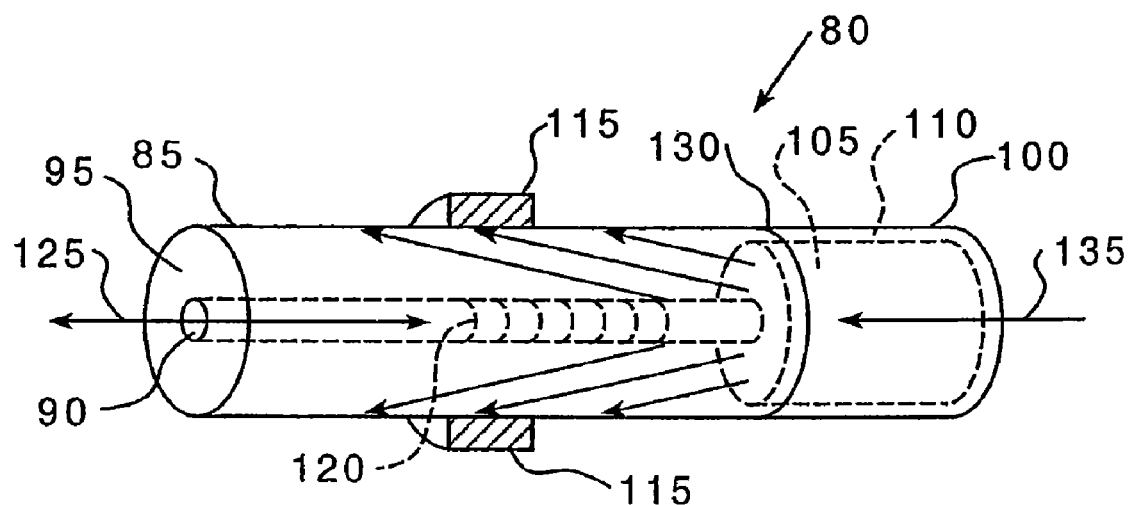
FIG. 8 is a partial cross-sectional side view of an optical fiber having a tunable in-fiber optic component according to a further alternate embodiment of the present invention.
Figure 9:
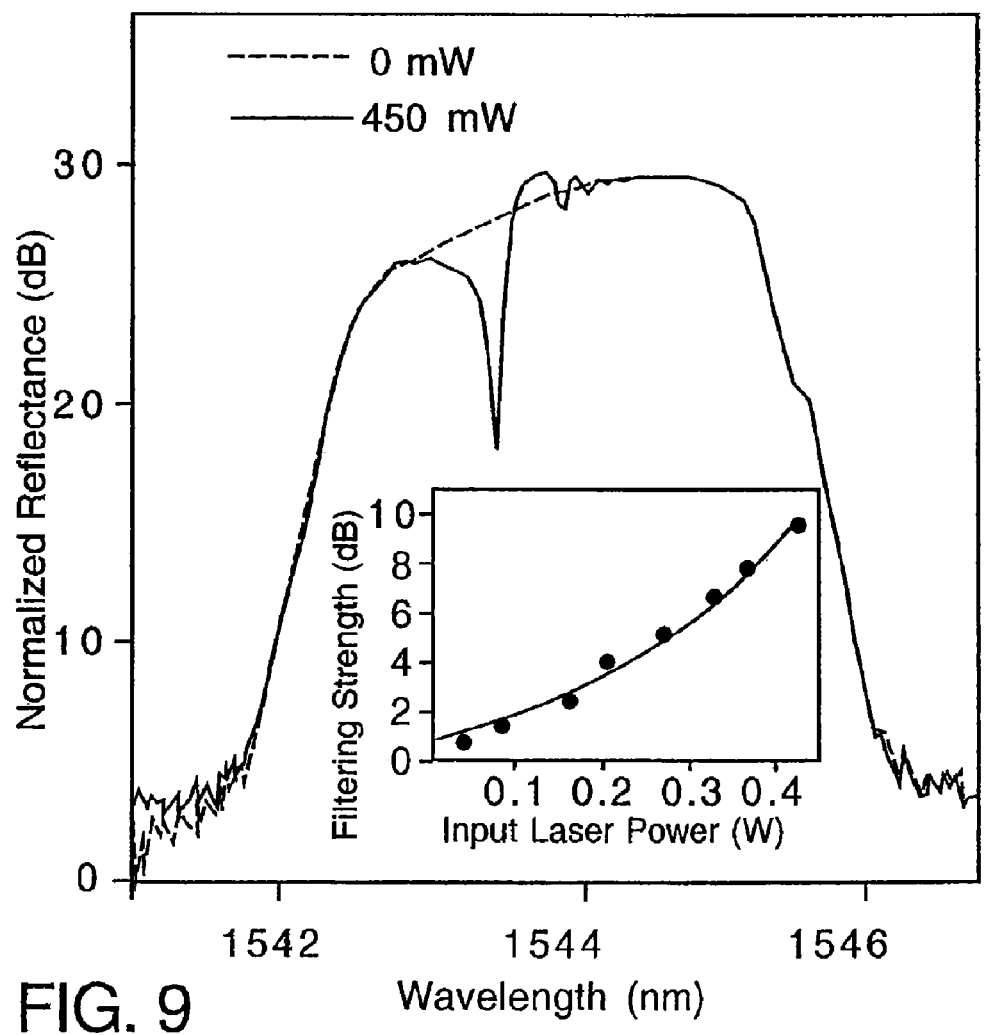
FIG. 9 is a graph illustrating the notch filter characteristics of an implementation of the optical fiber shown in FIG. 8.

According to a further alternate embodiment of the present invention, shown in FIG. 8, a small local refractive index change may be produced by generating a "hot spot" to modify the reflection spectrum of a chirped FBG. Specifically, in-fiber optical component 120 is, in this embodiment, a 4 cm long linear chirped FBG (1 nm/cm), and thermal coating 115 is an approximately 2 mm long silver film. In one implementation investigated by the inventor, the power light 135 was approximately 450 mW of 910 nm diode laser light. Power light 135 heated thermal coating 115, which in turn heated in-fiber optic component 120, thereby changing increasing the local refractive index of the portion of in-fiber optic component 120 near thermal coating 115 and expanding the grating period or periods. As a result, the resonance wavelength of the in-fiber optic component 120 at this point increased. As shown in FIG. 9, this localized heating created a notch filter in the FBG reflection spectrum.

Figure 10A:
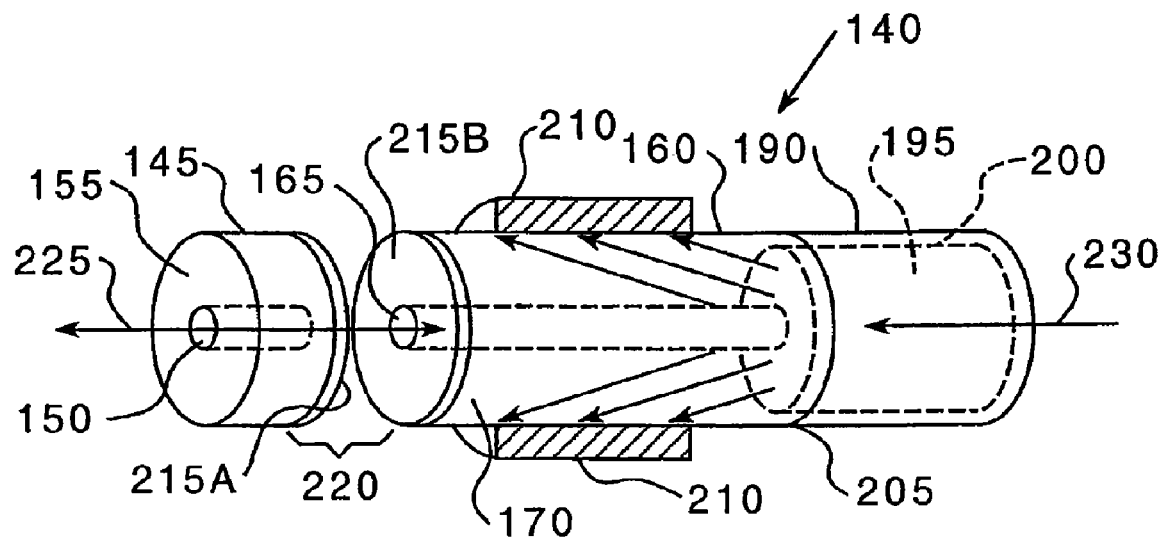
FIGS. 10A and 10B are a partial cross-sectional side view and a side view, respectively, of a fiber optic system according to a further alternate embodiment of the present invention.
Figure 10B:
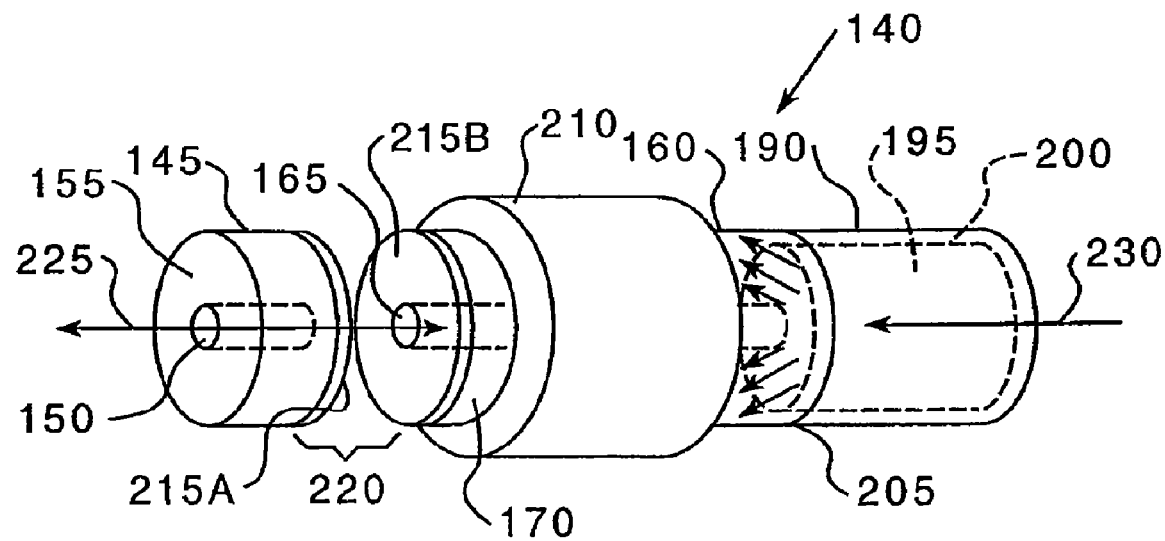

FIGS. 10A and 10B are side views of optical fiber system 140 according to still a further alternate embodiment of the present invention. As described below, optical fiber system 140 provides a dynamic Fabry-Perot micro-cavity resonator. Fiber optical Fabry-Perot micro-cavity resonators are utilized as an important optical component in fiber optic communication networks and fiber optic sensing systems. The present invention, among other applications, may be utilized to either stabilize the reflection spectrum of a Fabry-Perot micro-cavity resonator from random temperature or stress-induced drifting or to introduce a periodic phase change to the cavity for phase-locking signal detection. As seen in FIGS. 10A and 10B, optical fiber system 140 includes first single mode fiber portion 145 having core 150 and cladding 155. Optical fiber system 140 also includes second single mode fiber portion 160 having a core 165 and cladding 170 that is joined to, such as by fusion splicing, multimode fiber portion 190 having core 195 and cladding 200. Optical fiber system 140 includes an optical transducing element in the form of thermal coating 190 which is similar in structure to thermal coating 60 shown in FIGS. 2A and 2B. Thermal coating 190 is provided around at least a part of, and preferably the entirety of, the circumference of second single mode fiber portion 160.

As is known in the art, a Fabry-Perot filter is a high-spectral resolution (narrow-band-pass) optical filtering device that operates on the property of destructive light interference. A Fabry-Perot filter includes a cavity bounded on each side by two generally flat, transparent plates that have a partially reflective coating provided thereon. Typically, the cavity is filled with a dielectric material, which may include, without limitation, air. Incident light is passed through the two coated reflecting plates. The distance between the reflective coatings determines which wavelengths will destructively interfere and which wavelengths will be allowed to pass through the coated plates. In addition, the optical transmission spectrum of a Fabry-Perot filter typically shows multiple peaks with narrow passband width. The spacing between neighboring peaks is primarily determined by the gap between the two reflecting plates that form the cavity and the dielectric function of the material present in the cavity. As seen in FIGS. 10A and 10B, a partially reflective plate 215A is provided at the end of the first single mode fiber portion 145 and a partially reflective plate 215B is provided at the end of the second single mode fiber portion 160 opposite partially reflective plate 215A such that a cavity 220 is provided therebetween.

Figure 11:
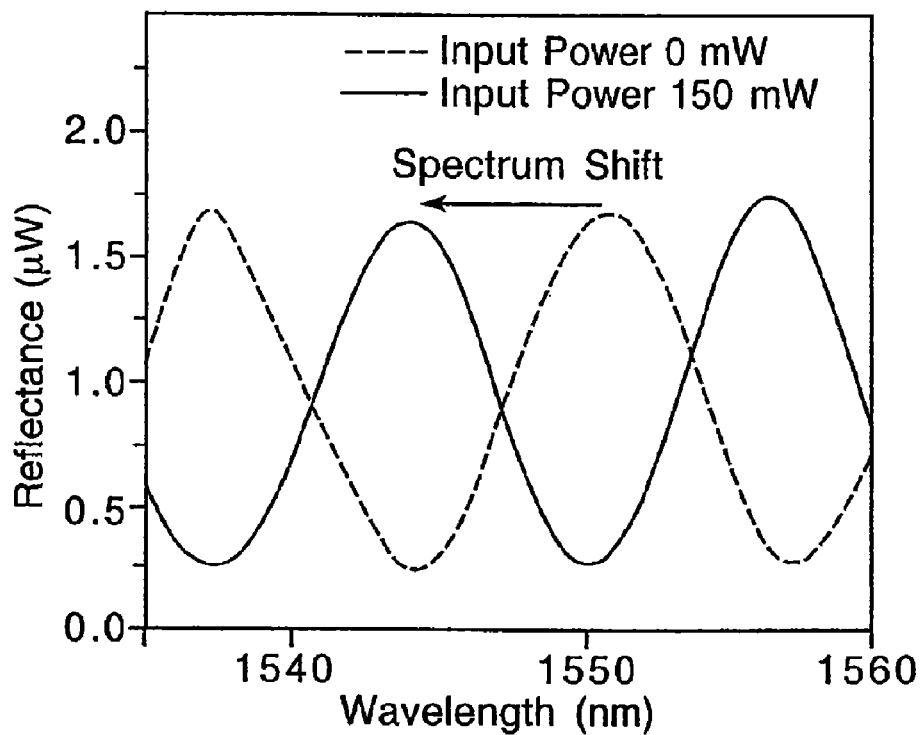
FIG. 11 is a graph illustrating a spectrum shift of an implementation of the fiber optic system shown in FIGS. 10A and 10B.

A sensing light 225 is directed through core 150 as shown in FIGS. 10A and 10B. Second single mode fiber portion 160 and multimode fiber portion 190 are joined to one another at junction 205. As shown in FIGS. 10A and 10B, junction 205, and in particular the different diameters of core 165 and core 195, act as an optical tap region that allows power light 230 that is directed through and propagates through core 195 to leak out of core 195 and into cladding 170, where it is ultimately absorbed by thermal coating 210. The absorbed power light 230 heats thermal coating 210, which in turn heats second single mode optical fiber 160. The heating of second single mode fiber 160 causes its length to increase, thereby decreasing the width of cavity 220 and changing the characteristics of the Fabry-Perot filter implemented by partially reflective plates 215A and 215B and cavity 220. In particular, the addition of power light 230 will cause the reflection spectrum of sensing light 225 to be shifted as demonstrated in FIG. 11.

Real-time gas and liquid flow sensing has many important applications in, for example, aerodynamics, combustion engine design, medical devices (such as respiratory devices) and chemical analysis. At present, state-of-the-art flow sensors are mostly based on MEMS technology. Although MEMS-based devices have been found to be effective, the packaging cost is relatively high, the packaged devices are typically relatively bulky, and they rely on external electrical power. As a result, the implementation of MEMS-based flow sensors in small diameter flow tubes (as required in respiratory devices) and in harsh environments is currently not feasible.

As an alternative, according to another aspect of the present invention, a tunable (active) optical fiber system including an FBG type in-fiber optic component powered by in-fiber light such as is shown in FIGS. 2A and 2B or 4A and 4B may be utilized to sense real-time gas and liquid (fluid) flow. In particular, if the FBG comprising in-fiber optic component 55 (FIGS. 2A and 2B) or in-fiber optic component 120 (FIGS. 4A and 4B) is heated as described herein such that the temperature thereof is higher than the surrounding environment, and if a gas or liquid is caused to flow past the associated optical fiber 30 or 80, the thermal energy removed from the FBG (in-fiber optic component 55 or 120) as represented by the resulting temperature change will depend on the flow rate of the surrounding gas or liquid. As a result, the flow rate can be measured by measuring the resonance wavelength shift(s) of the FBG that, as described above, are dependent upon FBG temperature changes. Resonance wavelength shifts due to fluid flow may be correlated to flow rates using known methods.

Figure 12:
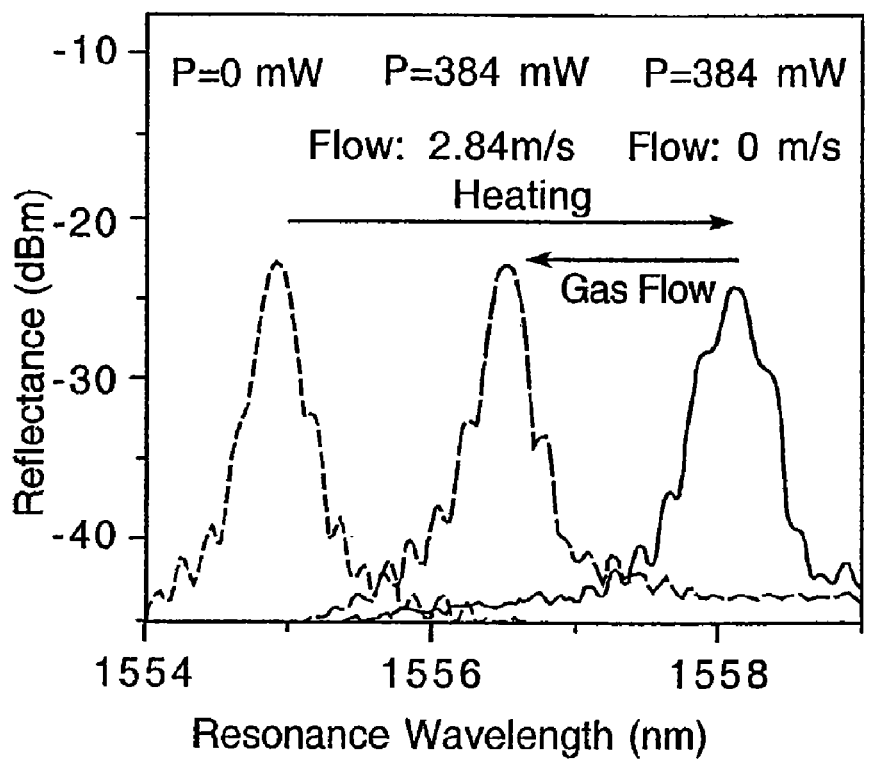
FIG. 12 is a graph illustrating operation of a fluid flow sensor according to an aspect of the present invention.

In one example implemented by the inventor, optical fiber 30 was provided with an in-fiber optic component 55 consisting of a 5 mm uniform FBG having a resonance wavelength of about 1553.7 nm at room temperature as shown in FIG. 12. Power light 75 consisting of 384 mW diode laser light was then provided, causing the resonance wavelength of the FBG to shift to about 1558.2 nm as shown in FIG. 12. Air was then caused to flow around optical fiber 30 at about 2.84 m/s, which cooled optical fiber 30 down and removed heat from the FBG, thereby causing another shift in the resonance wavelength to about 1556.6 nm as shown in FIG. 12.

Figure 13:
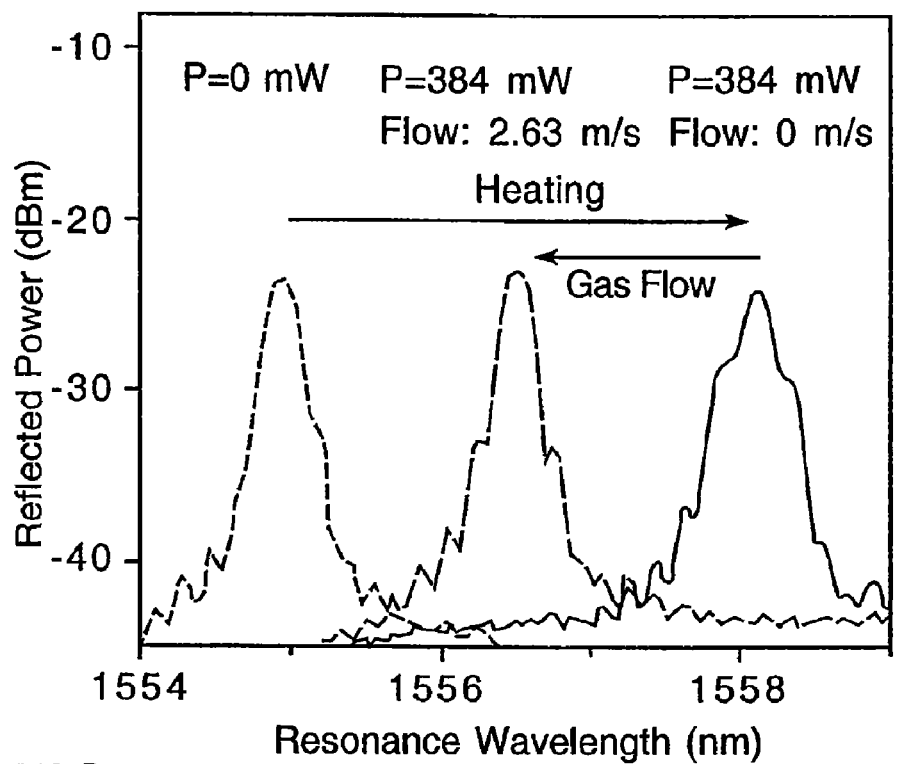
FIG. 13 is a graph illustrating operation of a flow sensor according to another aspect of the present invention.
Figure 14:
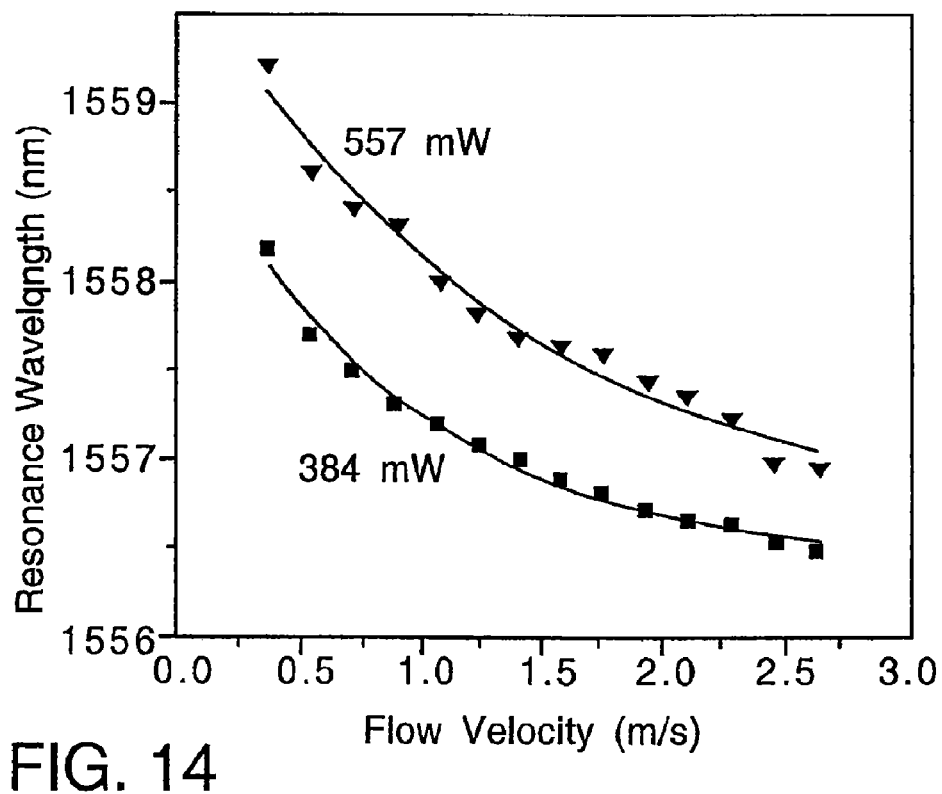
FIG. 14 is a graph that shows the resonance wavelength shifts as a function of fluid flow velocity of the flow sensor the operation of which is demonstrated in FIG. 13.
Figure 15:
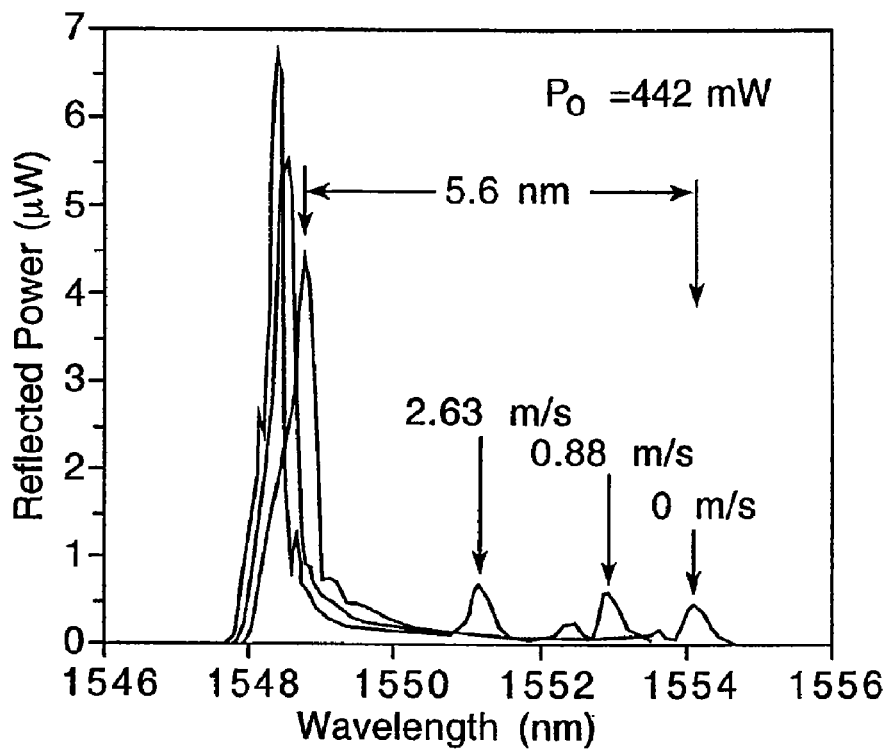
FIG. 15 is a graph that shows the spectral evolution of a particular flow sensor according to the present invention.
Figure 16:
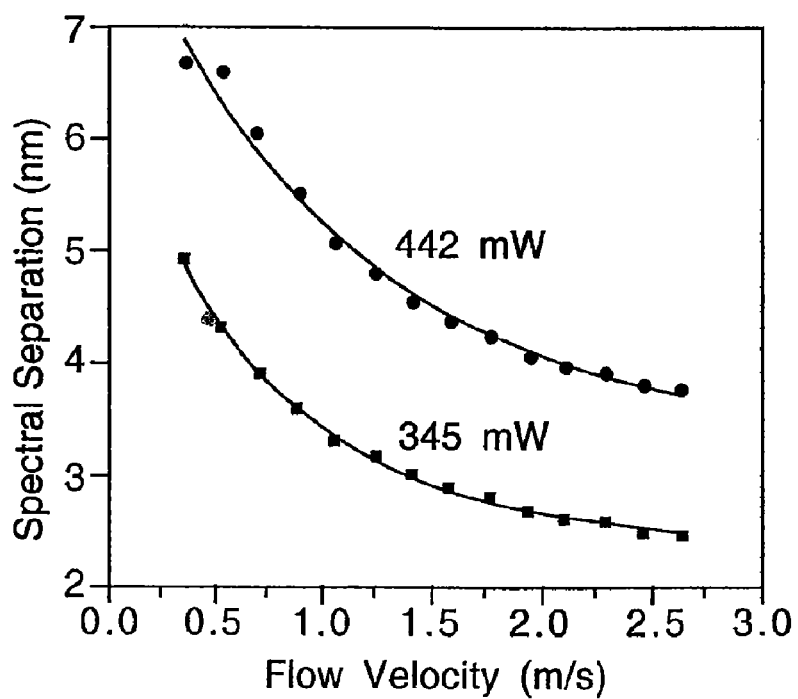
FIG. 16 is a graph that shows the spectral separation produced by a particular fluid flow sensor according to the present invention.

In another example implemented by the inventor, optical fiber 30 was provided with an in-fiber optic component 55 consisting of a 5 mm uniform FBG having a resonance wavelength of about 1554.9 nm at room temperature as shown in FIG. 13. Power light 75 consisting of 384 mW diode laser light was then provided, causing the resonance wavelength of the FBG to shift to about 1558.2 nm as shown in FIG. 13. $N_2$ was then caused to flow around optical fiber 30 in a direction perpendicular to the FBG at about 2.63 m/s, which cooled optical fiber 30 down and removed heat from the FBG, thereby causing another shift in the resonance wavelength to about 1556.5 nm as shown in FIG. 13. FIG. 14 shows the resonance wavelength shifts of the 5 mm uniform FBG as a function of flow velocity using a power light 75 at two different levels, 384 mW and 557 mW. As seen, the resonance wavelength shifts closely follow a simple exponential decay function of the $N_2$ velocity. Similar flow measurements were also carried out on an in-fiber optic component 55 consisting of a 1.7 cm uniform FBG having a resonance wavelength of about 1538.3 nm at room temperature. As discussed elsewhere herein, the magnitude of leaking power light 75 falls off exponentially with distance from the junction 130, thereby causing a temperature gradient in longer FBG such as the 1.7 cm uniform FBG just described. FIG. 15 shows the spectral evolution of such a 1.7 cm uniform FBG heated with a 442 mW power light 75 under $N_2$ flow velocities of 0.88 m/s and 2.63 m/s. FIG. 16 shows the spectral width of the 7 cm uniform FBG as a function of flow velocity using a power light 75 at two different levels, 345 mW and 442 mW. As seen in FIG. 16, the spectral widths decrease exponentially with the increase in flow velocity.

Figure 17:
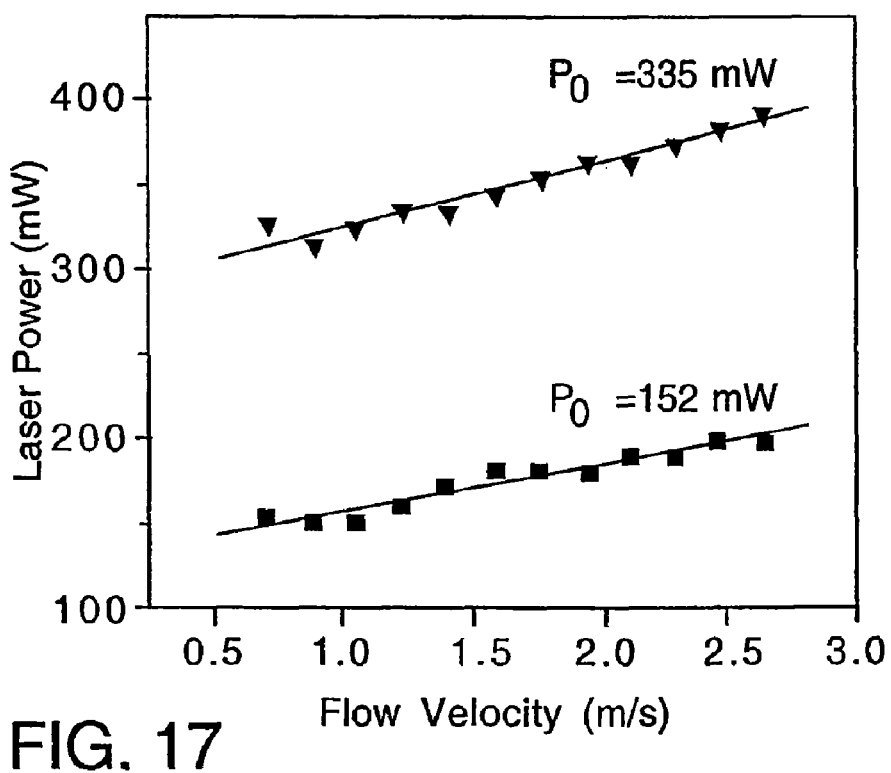
FIGS. 17 and 18 are graphs that demonstrate the operation of a particular fluid flow sensor according to the present invention in a constant wavelength (variable power) mode.
Figure 18:
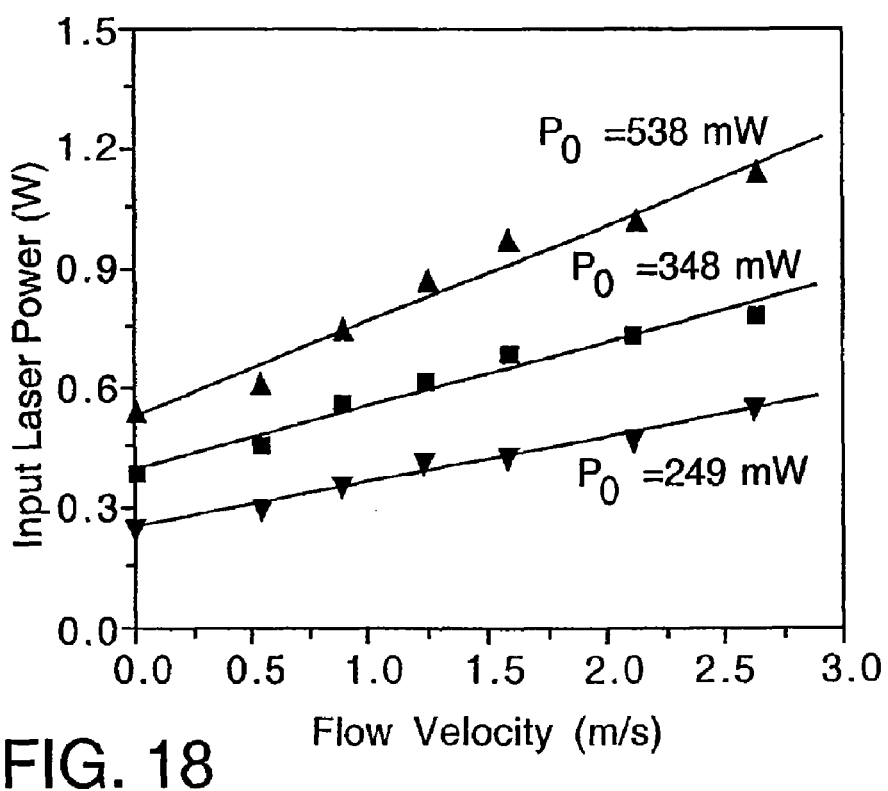

In addition, as will be appreciated, such a flow sensor may be operated in a constant power mode or a constant wavelength mode. In the constant power mode, a power light 75 or 135 having a constant power level is provided, and, as just described, flow rate is measured based on resonance wavelength shifts. In contrast, in the constant wavelength mode, flow rate is measured based on the power level(s) of power light 75 or 135 that is/are required to keep the resonance wavelength of the FBG constant (equal to some pre-set, pre-flow value) when liquid or gas flows thereby. FIGS. 17 and 18 demonstrate operation in the constant wavelength (variable power) mode. Specifically, FIG. 17 shows the power levels of power light 75 that are required to maintain a constant resonance wavelength at various flow velocities with initial power light levels of 152 mW and 335 mW using the 1.7 cm uniform FBG described above. Similarly, FIG. 18 shows the power levels of power light 75 that are required to maintain a constant resonance wavelength at various flow velocities with initial power light levels of 249 mW, 348 mW and 538 mW using the 5 mm uniform FBG described above. As seen in FIGS. 17 and 18, the power levels needed to maintain a constant, pre-set resonance wavelength follow linear functions with the flow velocity.

Figure 19:
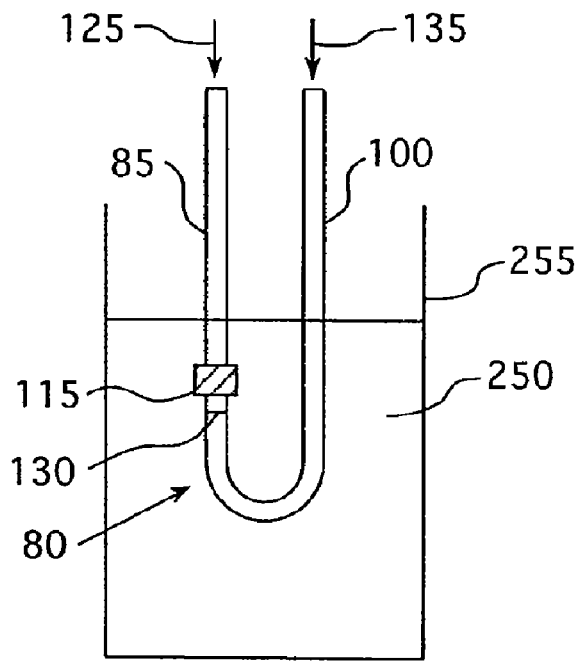
FIG. 19 is a schematic diagram of a tunable (active) optical fiber system including an FBG type in-fiber optic component powered by in-fiber light that may be utilized as a liquid level sensor according to a further aspect of the present invention.
Figure 20:
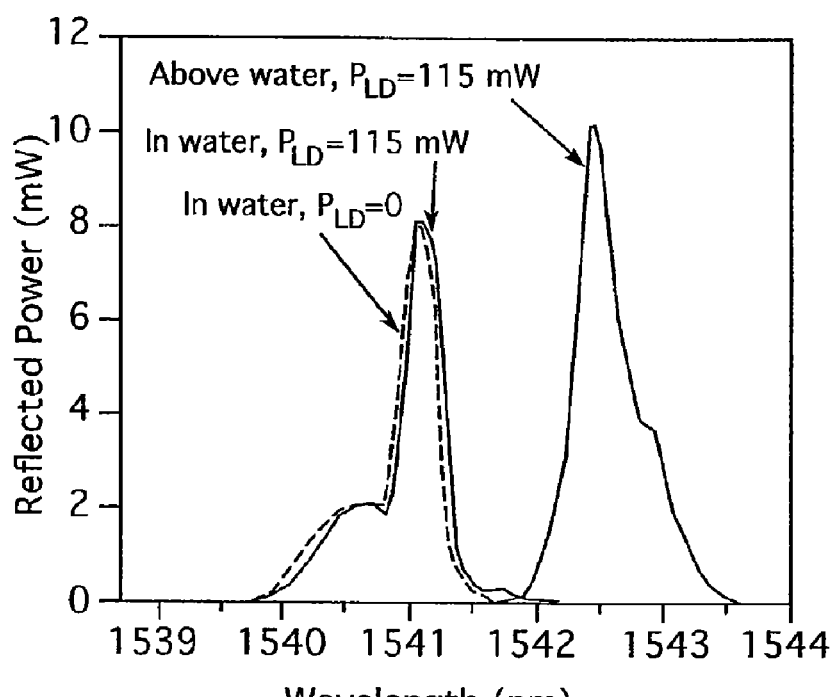
FIG. 20 is a graph that shows the spectral response of the FBG of the optical fiber system of FIG. 19 under certain conditions.

As a further alternative, according to yet another aspect of the present invention, a tunable (active) optical fiber system including an FBG type in-fiber optic component powered by in-fiber light such as is shown in FIGS. 2A and 2B or 4A and 4B may be utilized as a liquid level sensor to monitor the level of a liquid in a container, such as, for example, and without limitation, the level of liquid hydrogen in cryogenic fuel tanks for space missions. One example of such an implementation is shown in FIG. 19. As seen in FIG. 19, an optical fiber 80 as described in connection with FIGS. 4A and 4B is used to monitor the level of water 250 contained in tank 255. Optical fiber 80 includes single mode fiber portion 85 (having a core and cladding (not shown)) that is joined to, such as by fusion splicing, multi-mode fiber portion 100 (having a core and cladding (not shown)) at a junction 130. Optical fiber 80 also includes thermal coating 115 and an in-fiber optic component (surrounded by thermal coating 115 and not shown in FIG. 19) in the form of a uniform 5 mm FBG. A sensing light 125 is directed through the core of single mode fiber portion 85 and a power light 135 (comprising ten watts of 910 nm laser light from a high power diode laser array) is directed through the core of multi-mode fiber portion 100. As described in connection with FIGS. 4A and 4B, junction 130 acts as an optical tap region that allows a portion of power light 135 to leak out of the core and into of multi-mode fiber portion 100, where it is ultimately absorbed by thermal coating 115. The absorbed power light 135 heats thermal coating 115 which in turn radiates heat that is conducted therefrom and heats in-fiber optic component 120. FIG. 20 shows the spectral response of the FBG of the optical fiber 80 of FIG. 19 in: (i) water with no power light 135, (ii) in water with about 115 mW of power light 135, and (iii) in air with about 115 mW of power light 135.

To determine whether the FBG is submersed inside the water 250 inside tank 255 (level sensing), the 910 nm laser was turned on to inject 115 mW power light into multi-mode fiber portion 100 to heat the FBG. When the grating is submersed under the water 250, the resonance peak (solid trace) of the heated FBG is shifted about 60-pm from the unheated peak (dotted trace). When the FBG is pulled above the level of water 250, the FBG reflection peak rapidly shifted over about 1.4 nm from 1541 nm to 1542.4 nm as shown in the FIG. 20. This dramatic thermal response for the heated FBG thus provides unambiguous detection whether or not the FBG is immersed in the water 250. As will be appreciated, such an optical fiber 80 may be used to determine whether a liquid in a container such as tank 255 has fall below or risen above a particular level by positioning the FBG at the level of interest, heating the FBG with a power light 135, and monitoring the spectral response of the FBG.

Figure 21:
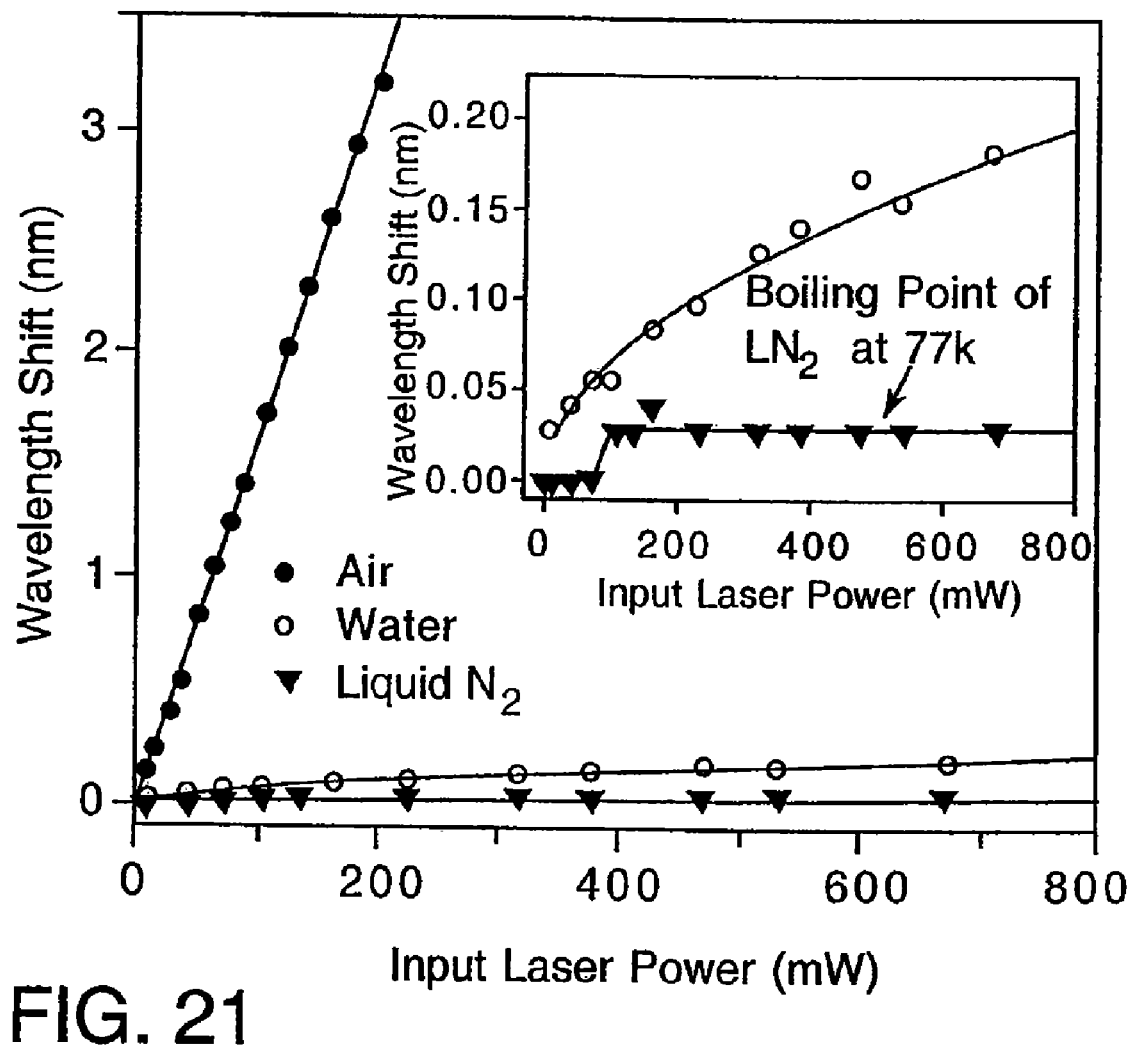
FIG. 21 is a graph that show the thermal responses of a heated grating, such as the FBG of optical fiber system shown in FIG. 19, in air, water, and liquid nitrogen at atmospheric pressure as a function of input laser power (power light) according to an aspect of the present invention.

The thermal responses of a heated grating, such as the FBG of optical fiber 80 shown in FIG. 19, in air, water, and liquid nitrogen as a function of input laser power (power light) are characterized in FIG. 21. As expected, the heated grating when exposed to air produced the largest resonance wavelength shift. The peak shift of the heated grating in ambient room temperature air follows a linear variation with input laser power with a slope of 15 pm per mW. A 10-mW laser input will produce a 150 pm reflection peak shift. This is in contrast to a 20 pm shift in water and a five pm shift in liquid nitrogen. The grating wavelength shifts in water and liquid nitrogen were re-plotted using a reduced vertical scale as shown in the inlet of FIG. 21.

Figure 22:
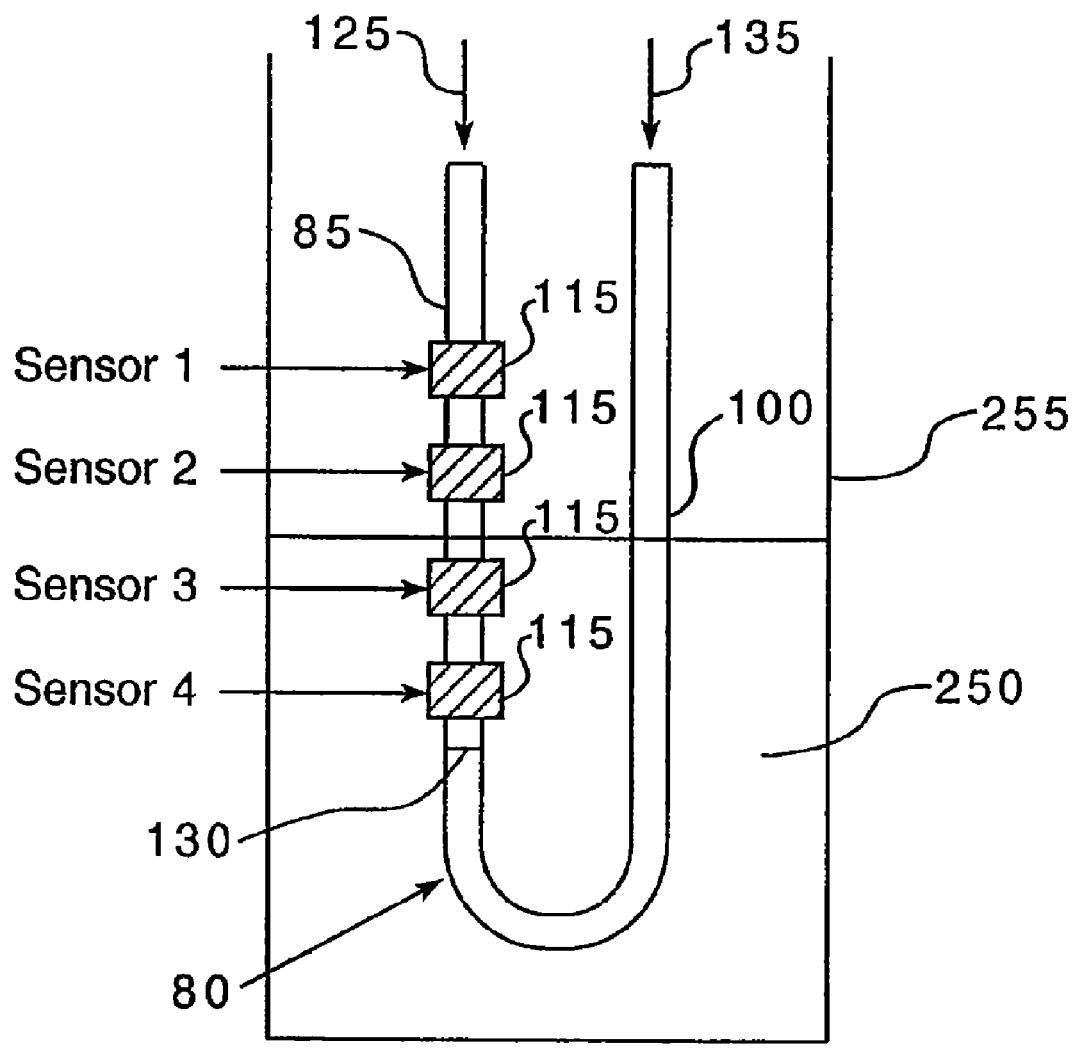
FIG. 22 is a schematic diagram of an alternative tunable (active) optical fiber system including multiple FBG type in-fiber optic components powered by in-fiber light that may be utilized as a liquid level sensor according to a further aspect of the present invention.

FIG. 22 is an alternate embodiment of an optical fiber 80 utilized as a liquid level sensor. The optical fiber of FIG. 22 is similar to the optical fiber 80 of FIG. 19 except that it includes four thermal coatings 115 (each surrounding a 5 mm uniform FBG) spaced 3 cm apart from one another along single mode fiber portion 85. For convenience, the FBGs shall be referred to as sensor 1, sensor 2, sensor 3 and sensor 4, with sensor 4 being located about 3 cm from junction 130. As seen in FIG. 22, sensor 1 has the shortest resonance wavelength and is the topmost FBG, and sensor 4 has the longest resonance wavelength is the lowest FBG. The optical fiber 80 of FIG. 22 can thus be used to sense the presence of liquid at four different locations, and as a result can sense four different liquid levels within a container such as tank 255.

Figure 23A:
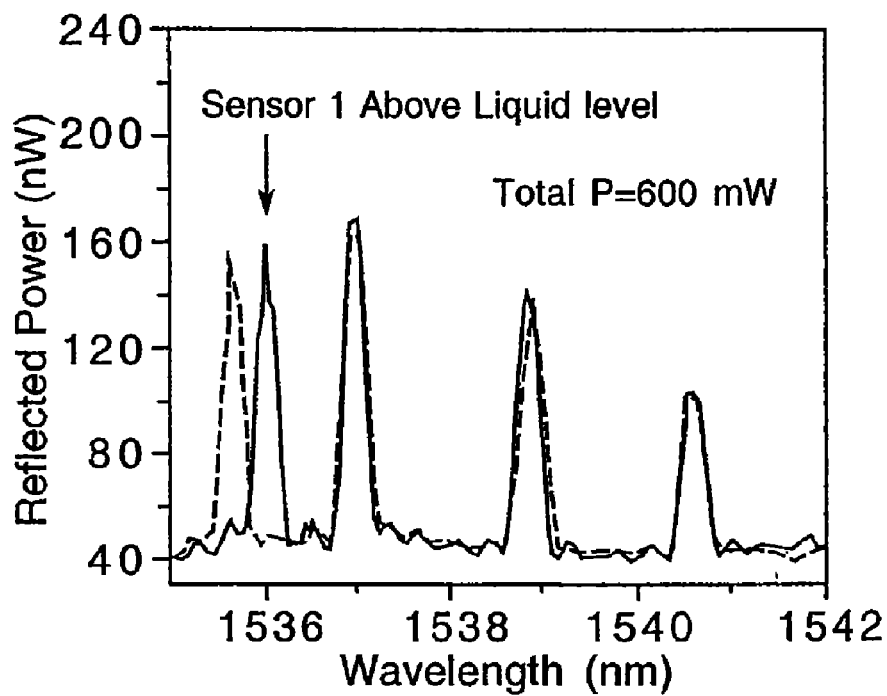
FIGS. 23A through 23D show the reflection spectrum of each of the FBGs of the optical fiber system of FIG. 22 under various conditions.
Figure 23B:
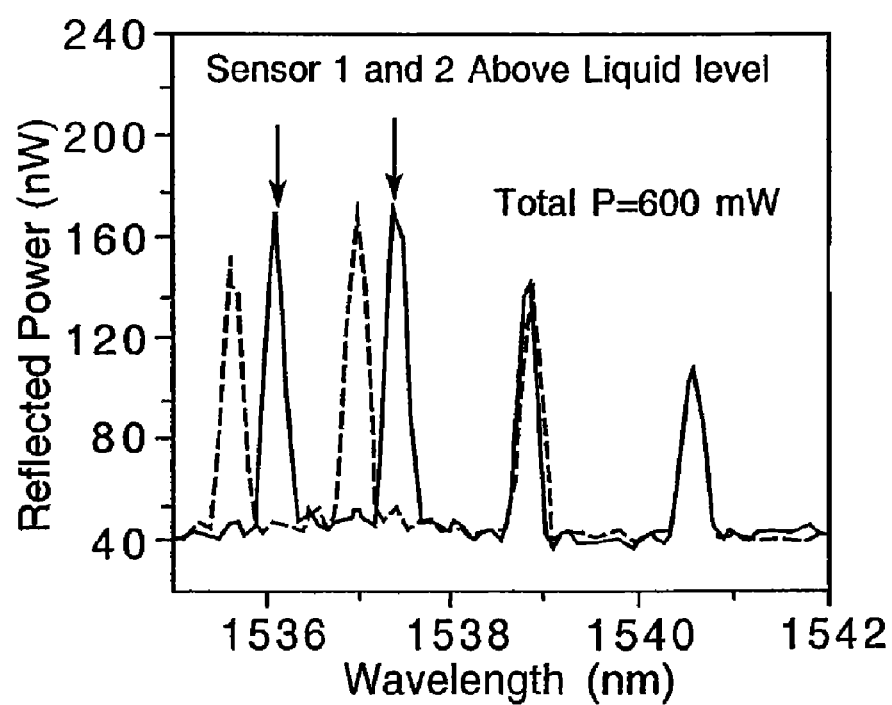
Figure 23C:
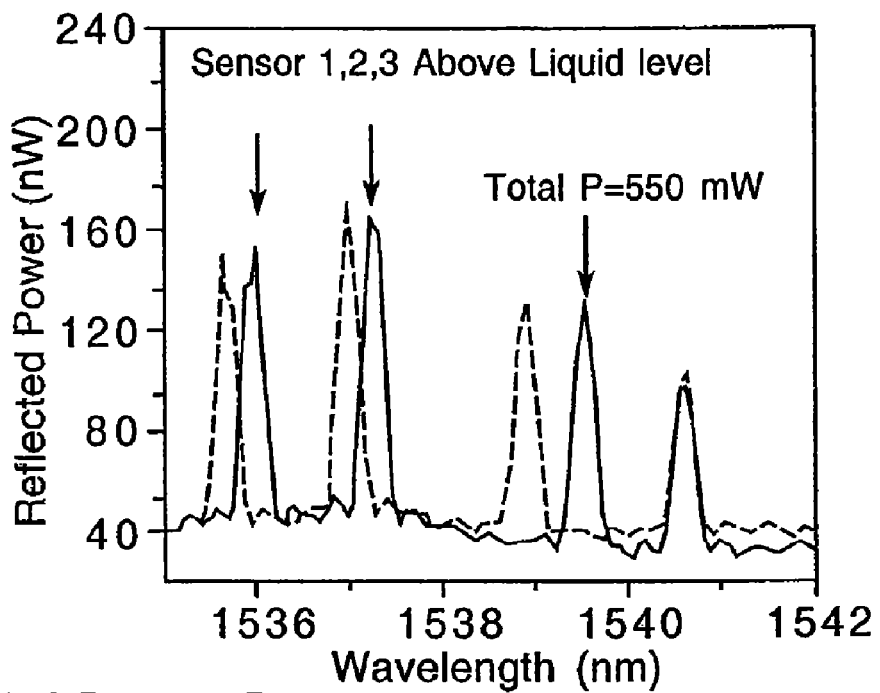
Figure 23D:
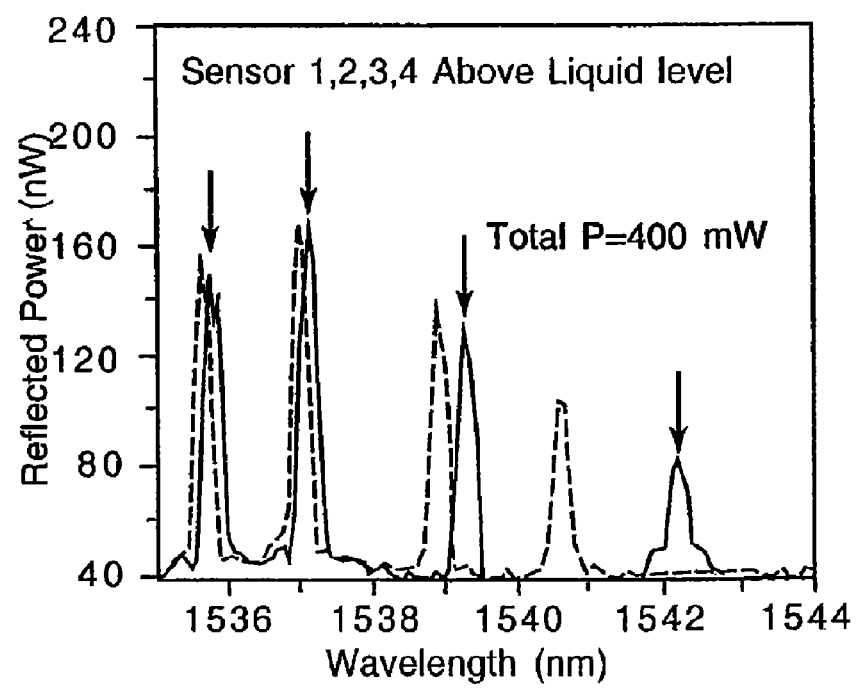

FIGS. 23A through D show the reflection spectrum of each FBG (sensors 1-4) in an unheated condition (no power light 135) in dotted line form. When the optical fiber 80 is pulled out from the water 250, sensor 1 is the first grating to rise above the water level and sensor 4 is the last to emerge. FIG. 23A shows the reflection spectrum of the heated FBG when sensor 1 is pulled out from the water with 600-mW input laser power (power light 135). The resonance peak for sensor 1 shifted 350 pm from 1535.7 nm to 1536.05 nm. Due to the much larger specific heat and thermal convection rates of water than those of air, reflection peaks for heated gratings remaining in the water shifted less than 10 pm. The dramatic resonance peak shift for sensor 1 above the liquid surface provides unambiguous detection of the liquid level. As shown in FIGS. 23B-23D, similar behavior is observed when sensors 2, 3 and 4 are pulled out from the water 250 in Succession. FIGS. 23C and 23D also show non-uniform peak shifts for the different FBGs while the input laser power (power light 135) is reduced to 550 mW and then to 400 mW. This is due to the non-uniform leakage profile in single mode fiber portion 85. The power is reduced to avoid the spectral deformation of sensor 4 due to overheating.

The level sensing applications have been described herein using optical fiber 80 as shown in FIGS. 4A and 4B. It should be understood, however, that this is for illustrative purposes and that other embodiments of the present invention, such as the optical fiber 30 shown in FIGS. 2A and 2B may also be used in level sensing applications.

Finally, the particular embodiments described above in connection with FIGS. 2-12 have been based on the conversion of the in-fiber power light (75, 135, 230) to thermal energy using an optical transducing element comprising a light absorbing thermal coating (60, 115, 210). However, the concept of the present invention is not limited to the conversion of the in-fiber power light to thermal energy. The in-fiber power light may also be converted to other energy types (that are then used to tune an in-fiber optic component), such as mechanical, acoustic, electrical, magnetic and optical (at other wavelengths) energy using various types of alternative transducing elements and energy conversion/harvesting mechanisms. For example, recent developments in the area of photo-mechanics have shown that polymer membranes containing light-sensitive molecules undergo rapid photo-contraction or expansion under weak polarized light radiation. In particular, recent investigations have shown that liquid-crystal membranes containing azobenzene chromeophore can be repeatedly bent without apparent fatigue. Such membranes may be provided on an optical fiber containing an in-fiber optic component, and bending, twisting, stretching and/or compressing of such membranes using in-fiber power light may be utilized to tune the in-fiber optic component (e.g., to change the spacing of the grating of an FBG or to deform a micro-mirror to adjust the Q-value and finesse of a micro-optical resonator). In this case, the membrane acts as an on-fiber actuator. In addition, such a membrane may be attached to a piezo actuator membrane to provide on-fiber optical-to-electrical conversion, without wires attached from the light transmitting end of the fiber. In addition, laser micro-machining of a thermal coating such as thermal coatings 60 and 115 will enable in-fiber optical energy to induce periodic index modulation to produce long period fiber grating filters for in-fiber power equalization.

Figure 24:
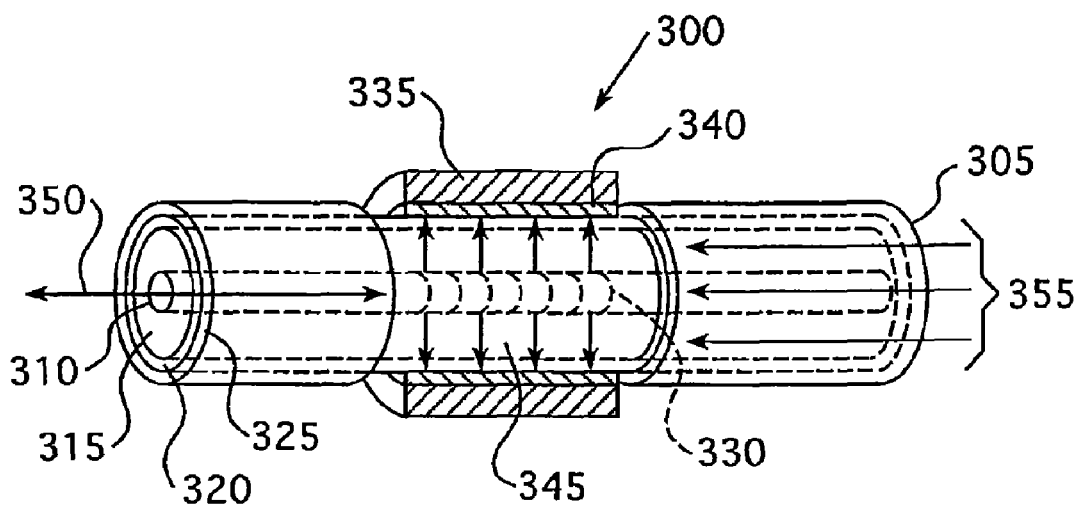
FIG. 24 is a side isometric view (in partial cross-section) of a hydrogen sensor according to a further embodiment of the present invention.

FIG. 24 is a side isometric view (in partial cross-section) of a hydrogen sensor 300 according to a further embodiment of the present invention. As seen in FIG. 24, the hydrogen sensor 300 includes an optical fiber 305 that includes a core 310, an inner cladding 315, an outer cladding 320 and a protective layer 325. Preferably, and as described elsewhere herein in connection with the optical fiber 30 shown in FIGS. 2A and 2B, the core 310, inner cladding 315 and outer cladding 320 are made of light propagating materials, wherein the core 310 has an index of refraction that is greater than the index of refraction of the inner cladding 315, which in turn is greater than the index of refraction of the outer cladding 320. Except as otherwise described herein, establishing the relative indices of refraction in this manner causes light propagating in core 310 to be confined therein, and light propagating in inner cladding 315 to be confined therein.

In one particular embodiment, the core 310 is made of a glass material such as fused silica that is doped with germanium and/or boron to increase the index of refraction thereof, the inner cladding 315 is made of fused silica, and the outer cladding 320 is made of fused silica that is doped with fluorine to decrease the index of refraction thereof. Particular dopant levels and indices of refraction may be as described elsewhere herein, such as in connection with the optical fiber 30 shown in FIGS. 2A and 2B. Alternatively, outer cladding 320 may be made of a polymer material such as clear silicone or PFA.

As seen in FIG. 24, the optical fiber 305 includes an FBG 330 written into the core 310 in a suitable manner, such as, without limitation, any of the manners described elsewhere herein. Alternatively, another type of wavelength resonant in-fiber optic component (i.e., a component that reflects particular wavelengths dependent on the characteristics of the component), such as, without limitation, a Fabry-Perot filter, may be employed instead of FBG 330. In addition, a palladium layer 335 is provided around at least a portion of and preferably the entirety of the outer circumference of the outer cladding 320 (the protective layer 325 has been removed at this location) in a position that is proximate to the position of the FBG 330 (FIG. 24 shows thermal coating 60 in partial cut-away to enable viewing of the other components of optical fiber 30). The palladium layer 335 is a layer of material that includes palladium, and may be palladium only or a palladium alloy. The palladium layer 335 acts as a hydrogen absorbing material for the reasons described below. As is known, when palladium is in the presence of ambient hydrogen, a chemical reaction occurs wherein palladium hydride is formed. In addition, during this reaction, the material expands. As a result, in the presence of ambient hydrogen, the palladium layer 335 will form palladium hydride and will expand and thereby induce strain in the optical fiber 305 at a location adjacent thereto. The magnitude of the expansion and thus the strain is dependent upon the amount of hydrogen that is absorbed. As is also known, palladium does not normally adhere well to glass materials. Thus, in the preferred embodiment, an intermediate layer 340 that adheres well to both glass materials and palladium, such as a glue metal, is first provided around at least a portion of and preferably the entirety of the outer circumference of the outer cladding 320, and then the palladium layer 335 is provided over the intermediate layer 340 as shown in FIG. 24. The palladium layer 335 and the intermediate layer 340 may be applied by any one of many known coating methods such as sputter coating, and may be thickened economically by electro or electroless plating.

Referring to FIG. 24, the optical fiber 305 also includes an optical tap region 345 located in a portion of the optical fiber 305 that is proximate to the palladium layer 335. As described elsewhere herein, the optical tap region 345 is a region of the optical fiber 305 that will allow certain light, as described in greater detail below, that is propagating through the optical fiber 305 to leak out of (i.e., be released from) the optical fiber 305 and be absorbed by the palladium layer 335. As described elsewhere herein, the optical tap region 345 may be created in a number of ways. For example, laser techniques or ion-implantation techniques may be used to, in effect, damage the inner cladding 315 in a selected region and thereby alter its index of refraction such that the power light 355 (described below) will leak out of the inner cladding 315 at the optical tap region 345.

In operation, as illustrated in FIG. 24, a sensing light 350 is directed through and propagates through the core 310. As is known in the art and as described elsewhere herein, the sensing light 350 will propagate through the core 310 and encounter the FBG 330, and a particular resonance wavelength will be reflected back in the opposite direction. In addition, as described above, the palladium layer 335 absorbs any ambient hydrogen and is caused to expand a certain amount depending upon the amount (concentration) of hydrogen that is present. The expansion of the palladium layer 335 will induce a strain in the optical fiber 305, which strain will stretch the core 310 (and the entire fiber) and thereby change the spacing of the gratings of the FBG 330. As also described elsewhere herein, the particular resonance wavelength that is reflected by an FBG depends upon the grating spacing. Thus, changes in the spacing of the gratings of the FBG 330 resulting from strain induced by the expansion of the palladium layer 335 will change the resonance wavelength that is reflected by the FBG 330. The spectral shifts (changes in the resonance wavelength that is reflected by the FBG 330) can thus be monitored and used to characterize and determine the ambient hydrogen content in the area proximate to the FBG 330 and palladium layer 335. However, as described in the "Background of the Invention" section herein, as the ambient temperature decreases (e.g., below, for example, a range of about 20-50 degrees C.), palladium absorbs hydrogen increasingly slowly, and, as a result, and without the improvement of this embodiment of the present invention described below, sensitivity would be low and response time would be increasingly slow (below one minute, up to hours or days) at any hydrogen concentration at such low temperatures, and in particular at relatively low hydrogen concentrations (e.g., below 4%).

Thus, according to an aspect of this embodiment of the present invention, a power light 355 is simultaneously directed through both the core 310 and the inner cladding 315 (or, alternatively, in just the inner cladding 315). Although the power light 355 is shown propagating in a direction opposite the sensing light 350, it may also be propagated in the same direction as sensing light 350. The power light 355 may be, for example, light generated from a high-power diode laser array (not shown). The power light 355 will, as seen in FIG. 24, propagate through the core 310 and the inner cladding 315 and will be confined therein until it reaches the optical tap region 345. When the power light 355 reaches the optical tap region 345, at least a portion of the power light 355 will leak out of the inner cladding 315 and into the outer cladding 320. The portion of the power light 355 that has leaked into the outer cladding 320 will then be transmitted substantially radially outwardly therefrom and will ultimately be absorbed by the palladium layer 335. The absorption of power light 355 by the palladium layer 335 induces heating of the palladium layer 335, which increases the temperature of palladium film and in turn increases the hydrogen absorption rate (and thus decreases the hydrogen absorption time) of the palladium in the palladium layer 335. As a result, the sensitivity and the response time of the hydrogen sensor 300 are increased, particularly at lower temperatures. In another embodiment, at least a portion of the power light may be absorbed by another part of the hydrogen sensor 300, such as a portion of the inner cladding 315 or the outer cladding 320. When the power light is so absorbed, heat will be generated which is then conducted to the palladium layer 335 to heat the palladium layer 335 and thereby increase the gas absorption rate.

Thus, as just described, the propagation of the power light 355 within the optical fiber 305 improves the performance of the hydrogen sensor 300 by heating the palladium layer 335. In one embodiment, the propagation of the power light 355 is continuous, thereby providing continuous heating of the palladium layer 335. However, as is known, the reaction between hydrogen and palladium that produces palladium hydride and expansion of the palladium layer 335 is relatively fast, on the order of a few seconds. Thus, while the continuous heating method described above will be effective, it will result in more power being used than is necessary as the heating is not required once the chemical reaction is complete. Thus according to another embodiment of the invention, a flash heating method is employed to improve the performance of the hydrogen sensor 300 at low temperatures (as described elsewhere herein) wherein power is conserved. That method is shown in the flowchart shown in FIG. 26.

Figure 26:
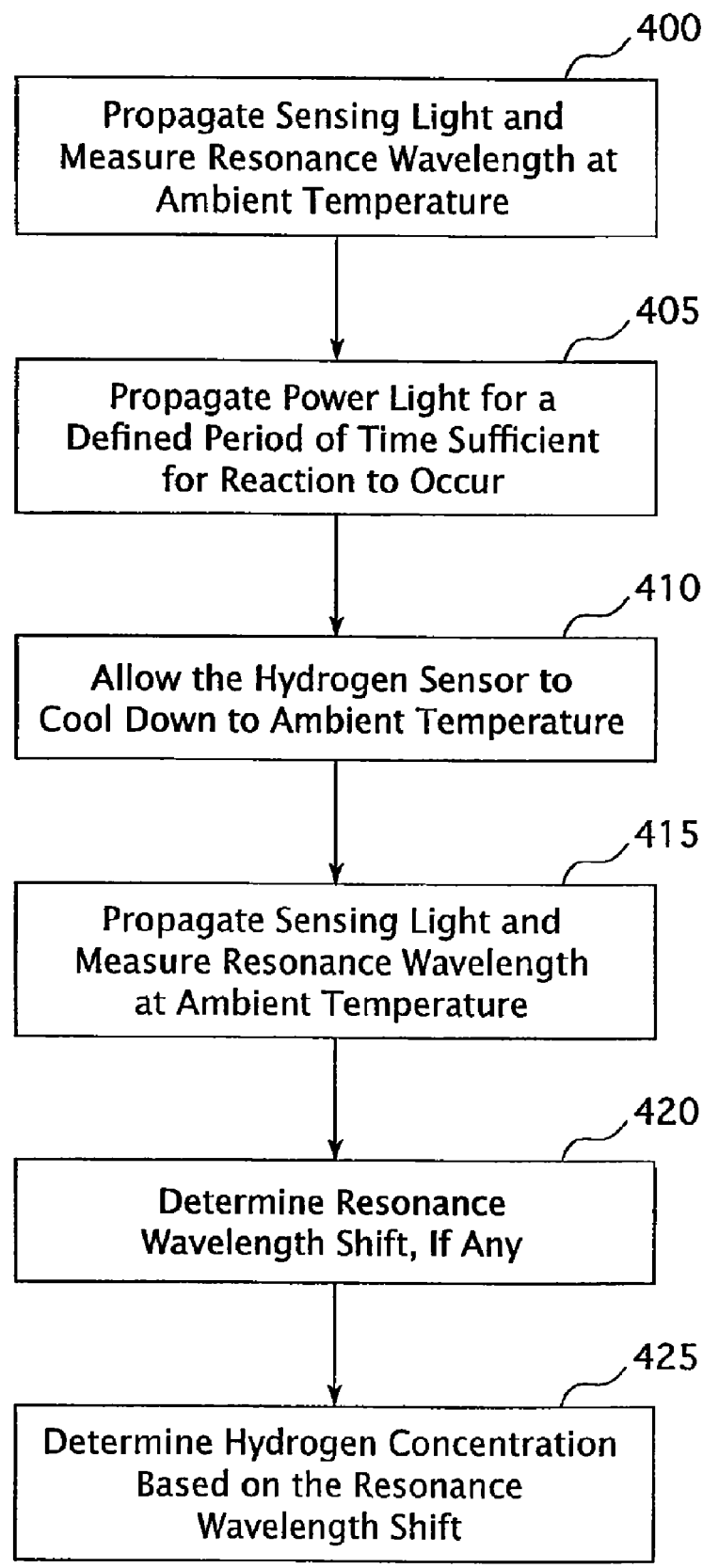
FIG. 26 is a flowchart of a flash heating method according to another embodiment of the invention that may be employed with the hydrogen sensors shown in FIGS. 24 and 25 to improve performance at low temperatures.

Referring to FIG. 26, the method begins at step 400, wherein the sensing light 350 is directed through the core 310 of the hydrogen sensor 300 at the ambient temperature (which may be a relatively low temperature on the order of –20 degrees C. or less) and the resonance wavelength that is reflected by the FBG 330 is measured. As described elsewhere herein, the hydrogen absorption by the palladium layer 335 at such low temperatures will be slow. Next, at step 405, the power light 355 is simultaneously directed through both the core 310 and the inner cladding 315 (or, alternatively, in just the inner cladding 315) for a defined period of time and then is shut off. During that time, when the power light 355 reaches the optical tap region 345, at least a portion of the power light 355 will leak out of the inner cladding 315 and into the outer cladding 320. The portion of the power light 355 that has leaked into the outer cladding 320 will then be transmitted substantially radially outwardly therefrom and will ultimately be absorbed by the palladium layer 335, thereby heating the palladium layer 335 and increasing the hydrogen absorption rate. The amount of time that the power light 355 is propagated is preferably just long enough for the reaction between the ambient hydrogen and the palladium in the palladium layer 335 to be completed (producing palladium hydride). That time may be, for example and without limitation, on the order of 10 seconds. Next, at step 410, the hydrogen sensor 300 is allowed to cool back down to ambient temperature. As will be appreciated by those of skill in the art, following the cool down, absorbed hydrogen is "locked in" the palladium layer 335 in the form of the palladium hydride. In other words, the cool down to ambient will not cause the reaction to be reversed. Then, at step 415, the sensing light 350 is once again directed through the core 310 of the hydrogen sensor 300 at the ambient temperature (it may be left on or turned off after step 400 and on again in this step) and the resonance wavelength that is reflected by the FBG 330 is once again measured. At step 420, the shift in the measured resonance wavelength that is reflected by the FBG 330, if any, is determined. As described elsewhere herein, if ambient hydrogen is present, its absorption by the palladium layer 335 will cause the palladium layer 335 to expand, thereby inducing a strain in the FBG 330 and a resulting resonance wavelength shift. Finally, at step 425, the ambient hydrogen concentration is determined based on the resonance wavelength shift (before and after the heating) due to the hydrogen absorption induced strain.

In addition, the hydrogen sensor 300 can be returned to its original, baseline form, so that it can be used again to make another measurement, by heating the palladium layer 335 using the power light 355 to an extent sufficient to "de-gas" the absorbed hydrogen (i.e., reverse the chemical process to convert the palladium hydride back to palladium and hydrogen). Once this is done, the palladium layer 335 will return to substantially its original size, thereby removing the hydrogen absorption induced strain and returning the spacing of the gratings of the FBG 330 to their original size (i.e., the FBG 330 will return to its original length). As a result, the resonance wavelength will return to its baseline level.

Figure 25:
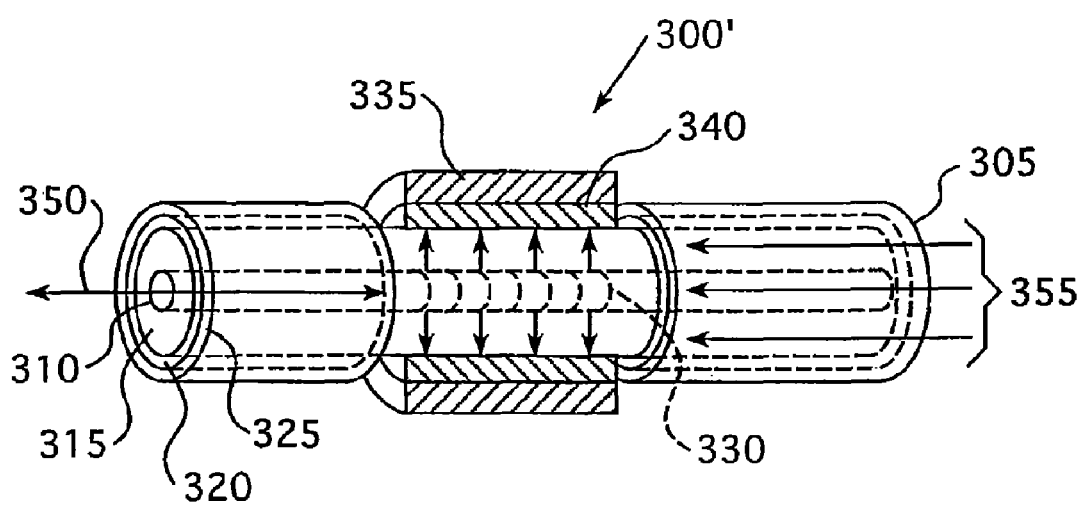
FIG. 25 is a side isometric view (in partial cross-section) of an alternative hydrogen sensor according to a further embodiment of the present invention.

FIG. 25 is a side isometric view (in partial cross-section) of a hydrogen sensor 300' according to an alternate embodiment of the present invention. The hydrogen sensor 300' is similar to the hydrogen sensor 300 except that, as seen in FIG. 25, in the hydrogen sensor 300', a portion of the outer cladding 320 is removed and the intermediate layer 340 and the palladium layer 335 are applied around the inner cladding 315. Since a portion of the outer cladding 320 is removed, the power light 355 will be permitted to leak out of the inner cladding 315 at that location and will be absorbed by the palladium layer 335 to provide the effect described above. The hydrogen sensor 300' may be used with either of the methods described herein (continuous heating or flash heating).

In one particular embodiment of the hydrogen sensor 300', the core 310 of the optical fiber 305 was a standard 8 μm fiber core with a N.A. of 0.12, and the outer cladding was a low-index plastic jacket having a N.A. of 0.48 to provide confinement of propagation of the power light 355 in the inner cladding 315. The protective coating 325 was an acrylate coating. To inscribe the FBG 330, the optical fiber 305 was first photosensitized via hydrogen loading for 1 week at 120 bars. After stripping a portion of the protective coating 325 and the outer cladding 320, a one-centimeter FBG 330 was written into the core 310 of the fiber 305 using a phase mask and a pulsed UV Excimer laser. Following grating fabrication, the fiber 305 was loaded into a magnetron sputtering machine. A fiber sputtering mount which allowed rotation of the fiber 305 during sputtering deposition was utilized to provide a uniform axial coating. To improve adhesion of the palladium forming the palladium layer to the silica surface of the inner cladding 315, a 20 nm layer of a glue metal was applied to the fiber 305 (to form the intermediate layer 340) followed by the much thicker (150-500 nm) palladium layer 335.

Testing of the hydrogen sensor 300' described above was performed in a sealed temperature-regulated chamber capable of maintaining −120-120° C. through the use of encapsulating liquid nitrogen cooling or recirculating fluid heating. Fiber feed-throughs were placed at either end of the chamber for sensor access. Two mass flow controllers provided a variable hydrogen and nitrogen mix for 0-10% $H_2$. Chamber pressure, temperature, and gas flow were monitored continuously.

The hydrogen sensor was then connected for testing and evaluation. The experimental setup can be found in K. P. Chen, L. J. Cashdollar, "Controlling Fiber Bragg Grating Spectra with In-Fiber Diode Laser Light," IEEE Phot. Technol. Lett., vol. 16, pp. 1897-1899, (2004), and id briefly described here. A high-power 910 nm diode laser (Qphotonics QLDM-910-1.5) was used to optically heat the fiber sensor. The diode laser is pigtailed with a 110-μm core multimode fiber. One end of the double-clad fiber containing the sensor was fusion spliced to the multimode fiber output of the diode laser. The other end of the double-clad fiber was spliced to a recirculator with a broadband light source, and a spectrum analyzer (Ando 6317B) for FBG sensor monitoring.

Figure 27:
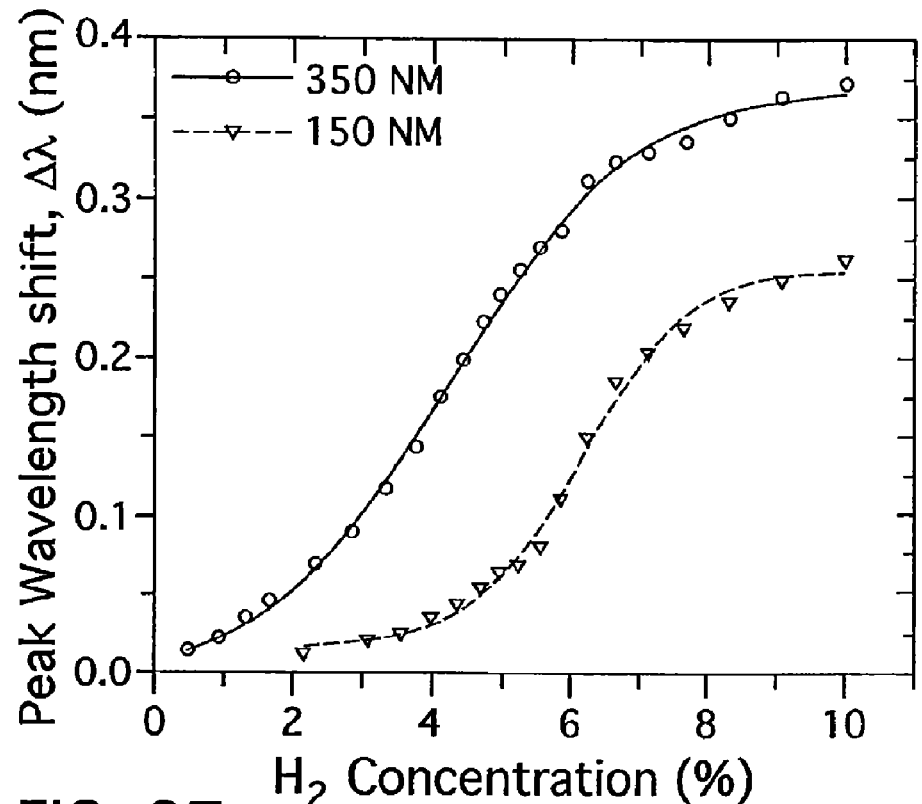
FIG. 27-30 are graphs demonstrating experimental results obtained by the inventors.

FIG. 27 shows the response of the Bragg wavelength to various hydrogen concentrations at room temperature. These measurements were performed for both 350-nm and 150-nm Pd coatings. The measurement was taken after 30 seconds of exposure to hydrogen. The thicker 350 nm Pd coated grating exhibits 0.37 nm response for 10% hydrogen, which shows 42.3% better response than 150-nm coating's response of 0.26 nm. The lowest tested hydrogen concentration was 0.5%, yielding 15 pm shift in the 350-nm Pd-coated FBG. The measurement was repeatable and showed little hysteresis at room temperature and low hydrogen concentrations. The sensor was also tested at the optimal temperature of 150° C., in which the 350-nm coated Pd-FBG shows a dramatic improvement in sensitivity and response time. The response time therein was found to be less than 9 seconds (instrument-limited). By replacing the broadband source and spectrum analyzer with a tunable laser, 0.125% hydrogen could be readily detected at 150° C.

Figure 28:
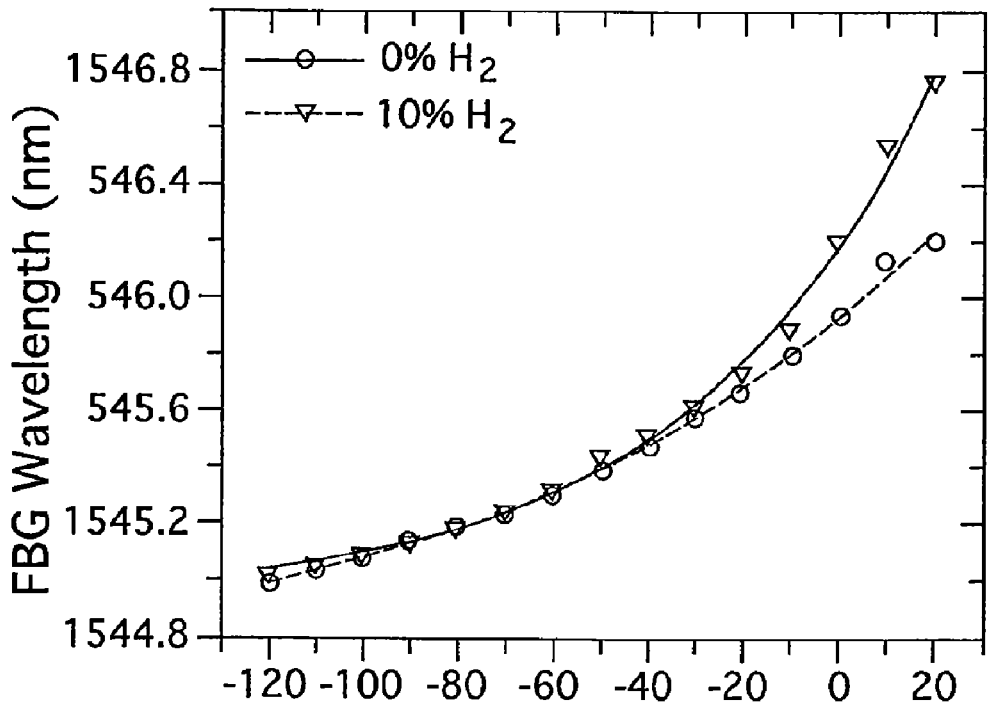

FIG. 28 explores the inherent problem associated with $H_2$ sensing at low temperatures. Herein, the 350 nm Pd coated sensor is exposed to 10% $H_2$ as the temperature is slowly raised while pausing for 30 s at each successive 10 degree increment and measuring the Bragg wavelength. The same test is repeated without hydrogen, and the two responses are compared. The response due to the presence of hydrogen is imperceptible until the temperature reaches about −20° C. This is because the absorption rate of hydrogen is extremely low at low temperatures.

Figure 29A:
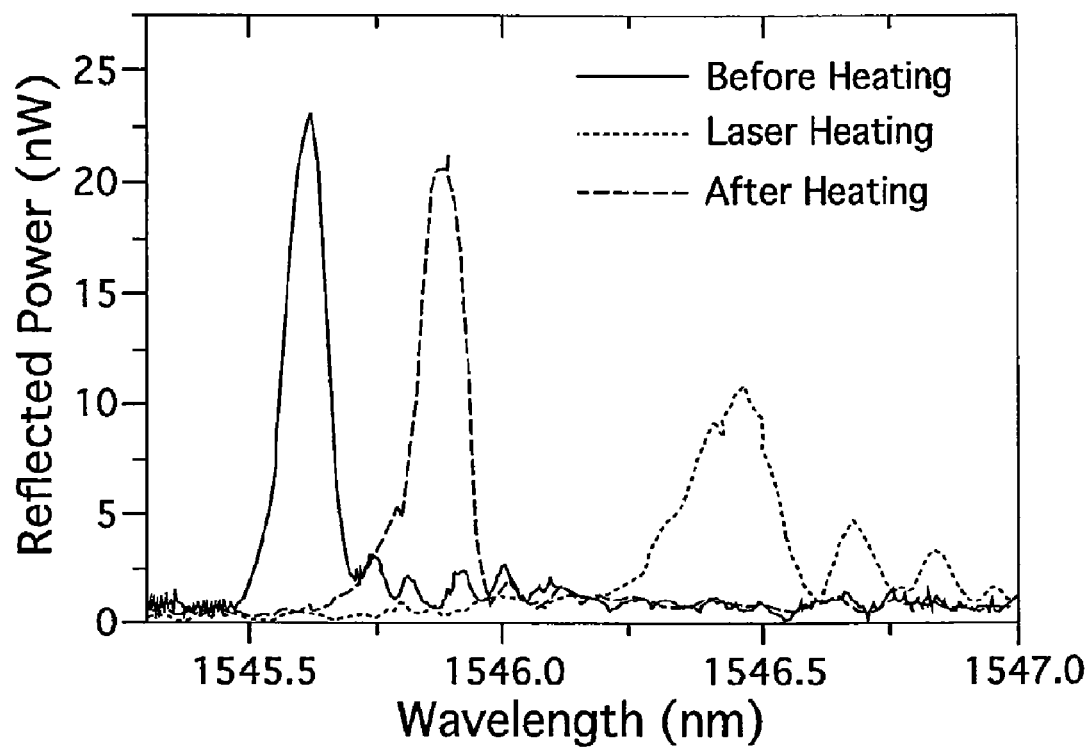
Figure 29B:
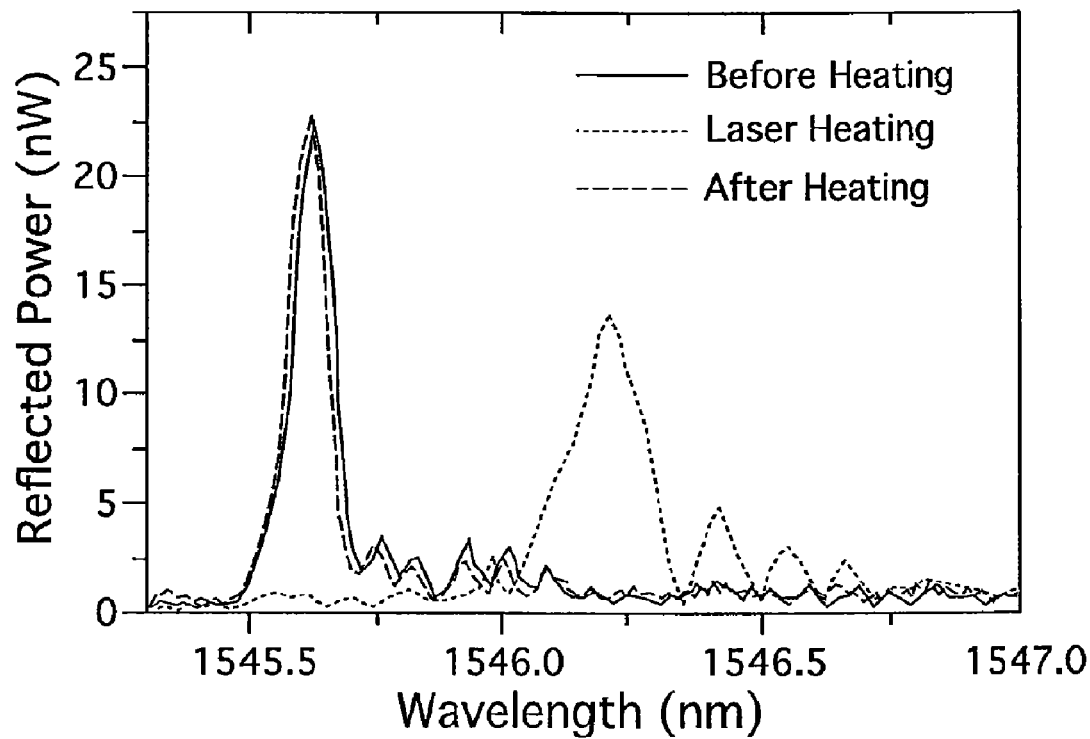

This problem can be readily solved by the active fiber sensor technology described herein and is demonstrated in FIGS. 29A and 29B. In a −50° C. environment, a passive 350-nm Pd-FBG sensor does not respond to 10% hydrogen in a reasonable time frame. However, since it is known that Pd-FBG sensors respond well at room temperature, according to the present invention, high-power diode laser light can be used to locally heat the FBG sensor to a temperature region in which sensors have reasonable responsivity. This is accomplished, in one embodiment, by stripping away the double clad fiber's outer coating; and re-coating with the Ta/Pd layers that serve to absorb the power light traveling in the inner cladding. This local sensor heating facilitates rapid hydrogen gas diffusion and reaction with the Pd film to form hydrides as shown in FIG. 29A. The heated FBG shows some spectral chirp, probably due to the non-uniform heating profile. The injection of 560 mW of laser power shifted the −50° C. FBG wavelength up from 1545.65 nm to 1546.45 nm, which corresponds to a sensor temperature of ~+10° C., determined from FIG. 28. Using a cut-back technique, it was estimated that 53% laser power was absorbed by the 2-cm long coating. After a brief 10-second laser heating, the laser is abruptly turned off and the sensor is allowed to cool rapidly to the ambient temperature, and the absorbed hydrogen is locked temporarily into the Pd film. A wavelength shift due to the $H_2$ absorption induced strain can be used to gauge the hydrogen concentration. At −50° C. the 350-nm Pd coated FBG shows 0.25 nm shift for 10% $H_2$ in FIG. 29A, which is approximately 67% of that at room temperature. This reduced responsivity is probably due to the FBG having a smaller thermo-optical coefficient at low temperatures. FIG. 29B serves as a comparison for this heating cycle, in which the same procedure is performed without the presence of hydrogen. Herein, the same thermal shift is noted due to the laser heating. However, after the heating is removed, the Bragg wavelength returns to its original position at the −50° C. ambient with no noticeable shift or deformation of the FBG reflection spectrum.

Figure 30:
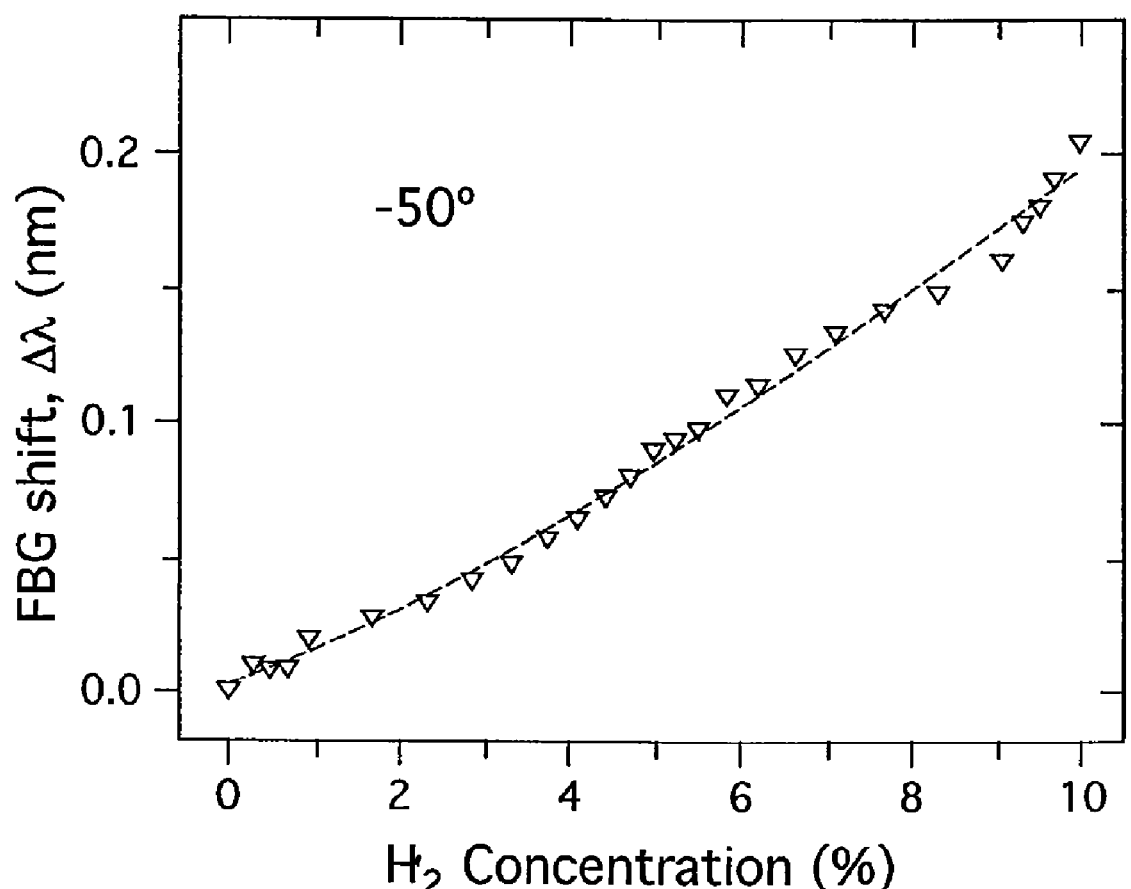

FIG. 30 illustrates the overall success of low temperature hydrogen leak detection using the in-fiber laser heating technique of the present invention. In this experiment, the ambient temperature is set at −50° C. while the hydrogen concentration is gradually increased. At each measured concentration, the heating laser is cycled on for 30 seconds, turned off, and the sensor response is measured. Full-scale response at −50° C. was approximately 50% to that at the room temperature, and the shape of the response curve is altered somewhat. In general, it was shown that relatively fast detection at low temperatures is possible using the laser heating technique of the present invention.

Thus, the experimental work described herein demonstrates an effective means to enhance the low-temperature performance of Pd-FBG sensors using the in-fiber optical heating technique of the present invention. By locally controlling the adsorption and degassing temperature of a Pd film, it is possible to shorten response time over a range of temperatures, thus facilitating fast operation of the hydrogen sensor at all temperatures. The technique described herein facilitates the construction of a FBG hydrogen sensor array with only one fiber and one feed-through. The elimination of electrical wires and the electricity traditionally used to heat the fiber sensor preserves all of the intrinsic advantages of fiber sensors and dramatically simplifies device packaging.

While specific embodiments of the invention have been described in detail, it will be appreciated by those skilled in the art that various modifications and alternatives to those details could be developed in light of the overall teachings of the disclosure. For example, although two embodiments of a hydrogen sensor have been shown and described herein, it will be appreciated that the present invention may be utilized to detect gasses other than hydrogen, in which case the palladium layer would be replaced by a gas absorbing material that experiences increased absorption of the gas in question when heated by the power light as described herein. Accordingly, the particular arrangements disclosed are meant to be illustrative only and not limiting as to the scope of the invention which is to be given the breadth of the claims appended in any and all equivalents thereof.

What is claimed is:

1. A method of sensing a gas at an ambient temperature, comprising:
    providing an optical fiber, wherein said optical fiber has a core, a wavelength resonant in-fiber optic component provided in said core at a first location, and at least one layer of a material attached to said optical fiber in proximity to said first location, said material being able to absorb said gas at a temperature dependent gas absorption rate, said gas absorption rate increasing when a temperature of said material is increased;
    propagating a first sensing light in said core at said ambient temperature, said wavelength resonant in-fiber optic component receiving said first sensing light and reflecting a first reflected light having a first resonance wavelength that is dependent on an ambient characteristic of said wavelength resonant in-fiber optic component;
    propagating a power light in said optical fiber for a defined period of time during which at least a portion of said power light is used to heat said material and cause said material to induce a strain in said optical fiber, said strain changing the ambient characteristic to a changed characteristic;
    allowing said material to cool to a temperature substantially equal to said ambient temperature after said defined period of time has expired;
    propagating a second sensing light in said core after said material is allowed to cool, said wavelength resonant in-fiber optic component receiving said second sensing light and reflecting a second reflected light having a second resonance wavelength that is dependent on said changed characteristic of said wavelength resonant in-fiber optic component;
    determining a difference between said first resonance wavelength and said second resonance wavelength; and
    using said difference to determine at least one of a presence of and a concentration of said gas.

2. The method according to claim 1, wherein said propagating a power light comprises propagating a power light in said optical fiber for a defined period of time during which at least a portion of said power light is released from said optical fiber at said first location and absorbed by said material, wherein said absorbed at least a portion of said power light heats said material and causes said material to induce a strain in said optical fiber, said strain changing the ambient characteristic to a changed characteristic.

3. The method according to claim 1, wherein said propagating a power light comprises propagating a power light in said optical fiber for a defined period of time during which at least a portion of said power light is absorbed at or about said first location, wherein said absorbed at least a portion of said power light heats said material and causes said material to induce a strain in said optical fiber, said strain changing the ambient characteristic to a changed characteristic.

4. The method according to claim 1, wherein said wavelength resonant in-fiber optic component is a fiber Bragg grating and wherein said ambient characteristic is a grating spacing of said fiber Bragg grating at said ambient temperature and wherein said changed characteristic is a grating spacing of said fiber Bragg grating following said step of allowing said material to cool.

5. The method according to claim 1, wherein said wavelength resonant in-fiber optic component is a Fabry-Perot filter and wherein said ambient characteristic is a length of at least a portion of said Fabry-Perot filter at said ambient temperature and wherein said changed characteristic is a length of at least a portion of said Fabry-Perot filter following said step of allowing said material to cool.

6. The method according to claim 1, wherein said gas is hydrogen and wherein said material includes palladium.

7. The method according to claim 6, wherein said material is palladium.

8. The method according to claim 6, wherein said material is a palladium alloy.

9. The method according to claim 6, wherein during said defined period of time a reaction occurs between said hydrogen and said palladium to produce palladium hydride, and wherein said reaction causes said at least one layer of a material to expand and induce said strain.

10. The method according to claim 9, wherein said defined period of time is long enough to allow said reaction to be completed.

11. The method according to claim 1, wherein said first sensing light and said second sensing light are portions of a continuously propagated light.

12. The method according to claim 1, wherein the step of propagating the first sensing light ends prior to said allowing step commencing and the step of propagating the second sensing light begins after said allowing step is completed.

* * * * *

UNITED STATES PATENT AND TRADEMARK OFFICE
CERTIFICATE OF CORRECTION

PATENT NO. : 7,792,392 B2  
APPLICATION NO. : 11/957746  
DATED : September 7, 2010  
INVENTOR(S) : Peng Chen et al.

Page 1 of 1

It is certified that error appears in the above-identified patent and that said Letters Patent is hereby corrected as shown below:

On the title page, Item (56), OTHER PUBLICATIONS, line 1, "characterization hydrogen" should read --characterization of hydrogen--.
Title page 2, Item (56), first column, OTHER PUBLICATIONS, line 4, "Voet et al." should read --Guemes et al., "Comparison of three types of fibre optic hydrogen sensors within the frame of CryoFOS project"--.
Title page 2, Item (56), first column, OTHER PUBLICATIONS, line 4, "Optical Optical Fibre" should read --Optical Fibre--.
Title page 2, Item (56), second column, OTHER PUBLICATIONS, line 5, "Coated Fier" should read --Coated Fiber--.
Title page 2, Item (56), second column, OTHER PUBLICATIONS, line 8, "Meas. Sci. Technol." should read --Institute of Physics Publishing, Meas. Sci. Technol.--.
Title page 2, Item (56), second column, OTHER PUBLICATIONS, line 14, "and Swtiches" should read --and Switches--.
Column 4, line 3, "out" should read --outer--.
Column 4, line 3, "generate" should read --to generate--.
Column 6, line 4, "show" should read --shows--.
Column 6, line 27, "FIG. 27-30" should read --FIGS. 27-30--.
Column 7, line 39, "is that is" should read --is that it--.
Column 8, line 30, "while)" should read --while--.
Column 13, line 48, "into of multi-mode" should read --into the multi-mode--.
Column 14, line 3, "has fall" should read --has fallen--.
Column 14, line 30, "length is" should read --length and is--.
Column 14, line 49, "Succession" should read --succession--.
Column 19, line 26, "and id" should read --and is--.
Column 20, line 23, "II$_2$" should read --H$_2$--.
Column 20, line 28, "is. performed" should read --is performed--.

Signed and Sealed this  
Seventeenth Day of July, 2012

David J. Kappos  
*Director of the United States Patent and Trademark Office*